United States Patent
Fung et al.

(10) Patent No.: US 10,499,856 B2
(45) Date of Patent: Dec. 10, 2019

(54) SYSTEM AND METHOD FOR BIOLOGICAL SIGNAL PROCESSING WITH HIGHLY AUTO-CORRELATED CARRIER SEQUENCES

(71) Applicant: Honda Motor Co., Ltd., Tokyo (JP)

(72) Inventors: Kin C. Fung, Dublin, OH (US);
Timothy J. Dick, Dublin, OH (US);
Charles William Hall, Jr., Hilliard, OH (US)

(73) Assignee: Honda Motor Co., Ltd., Tokyo (JP)

( * ) Notice: Subject to any disclaimer, the term of this patent is extended or adjusted under 35 U.S.C. 154(b) by 636 days.

(21) Appl. No.: 14/961,277

(22) Filed: Dec. 7, 2015

(65) Prior Publication Data

US 2016/0157783 A1 Jun. 9, 2016

Related U.S. Application Data

(63) Continuation-in-part of application No. 14/697,593, filed on Apr. 27, 2015, now Pat. No. 10,153,796.
(Continued)

(51) Int. Cl.
*G01N 33/48* (2006.01)
*G01N 33/50* (2006.01)
(Continued)

(52) U.S. Cl.
CPC .......... *A61B 5/7203* (2013.01); *A61B 5/0059* (2013.01); *A61B 5/7228* (2013.01); *G06F 19/36* (2013.01); *G08C 17/02* (2013.01)

(58) Field of Classification Search
None
See application file for complete search history.

(56) References Cited

U.S. PATENT DOCUMENTS

| 4,653,498 A | 3/1987 | New, Jr. et al. |
| 4,671,111 A | 6/1987 | Lemelson |

(Continued)

FOREIGN PATENT DOCUMENTS

| CN | 1798521 | 7/2006 |
| CN | 1802273 | 7/2006 |

(Continued)

OTHER PUBLICATIONS

Office Action of U.S. Appl. No. 14/851,753 dated Mar. 22, 2017, 14 pages.
(Continued)

*Primary Examiner* — Russell S Negin
(74) *Attorney, Agent, or Firm* — Rankin, Hill & Clark LLP

(57) ABSTRACT

A computer-implemented method for biological signal recording, including modulating a sampled evoked biological signal with a carrier sequence code resulting in a modulated evoked biological signal. The carrier sequence code has an autocorrelation function. The method includes demodulating the modulated evoked biological signal by calculating a convolution of the modulated evoked biological signal with the carrier sequence code resulting in an evoked biological signal spectrum. The evoked biological signal spectrum has a peak to sideband ratio as a function of the carrier sequence code. The method includes calculating deviations between each element of the sampled evoked biological signal and the peak to sideband ratio and filtering noise artifacts from the sampled evoked biological signal based on the deviations. Peak to sideband ratios may also be optimized by varying the sampling rate.

21 Claims, 11 Drawing Sheets

Related U.S. Application Data which is a continuation-in-part of application No. 13/858,038, filed on Apr. 6, 2013, now Pat. No. 9,272,689.

(51) Int. Cl.
  *A61B 5/00* (2006.01)
  *G06F 19/00* (2018.01)
  *G08C 17/02* (2006.01)

(56) References Cited

U.S. PATENT DOCUMENTS

| | | | |
|---|---|---|---|
| 4,891,764 A | 1/1990 | McIntosh | |
| 5,057,834 A | 10/1991 | Nordstrom | |
| 5,154,680 A | 10/1992 | Drzewiecki et al. | |
| 5,173,661 A * | 12/1992 | Knuttel | G01R 33/3875 |
| | | | 324/307 |
| 5,191,524 A | 3/1993 | Pincus et al. | |
| 5,195,606 A | 3/1993 | Martyniuk | |
| 5,369,601 A | 11/1994 | Tannenbaum | |
| 5,485,892 A | 1/1996 | Fujita | |
| 5,521,823 A | 5/1996 | Akita et al. | |
| 5,546,305 A | 8/1996 | Kondo | |
| 5,570,087 A | 10/1996 | Lemelson | |
| 5,609,158 A | 3/1997 | Chan | |
| 5,617,871 A | 4/1997 | Burrows | |
| 5,682,901 A | 11/1997 | Kamen | |
| 5,719,950 A | 2/1998 | Osten et al. | |
| 5,783,997 A | 7/1998 | Saitoh et al. | |
| 5,913,375 A | 6/1999 | Nishikawa | |
| 5,942,979 A | 8/1999 | Luppino | |
| 5,960,376 A | 9/1999 | Yamakado et al. | |
| 6,009,377 A | 12/1999 | Hiwatashi | |
| 6,026,340 A | 2/2000 | Corrado et al. | |
| 6,044,696 A | 4/2000 | Spencer-Smith | |
| 6,061,610 A | 5/2000 | Boer | |
| 6,104,296 A | 8/2000 | Yasushi et al. | |
| 6,172,613 B1 | 1/2001 | Deline et al. | |
| 6,185,487 B1 | 2/2001 | Kondo et al. | |
| 6,195,008 B1 | 2/2001 | Bader | |
| 6,198,996 B1 | 3/2001 | Berstis | |
| 6,256,558 B1 | 7/2001 | Sugiura et al. | |
| 6,271,745 B1 | 8/2001 | Anzai et al. | |
| 6,278,362 B1 | 8/2001 | Yoshikawa et al. | |
| 6,337,629 B1 | 1/2002 | Bader | |
| 6,361,503 B1 | 3/2002 | Starobin et al. | |
| 6,393,348 B1 | 5/2002 | Ziegler et al. | |
| 6,435,626 B1 | 8/2002 | Kostadina | |
| 6,438,472 B1 | 8/2002 | Tano et al. | |
| 6,459,365 B2 | 10/2002 | Tamura | |
| 6,485,415 B1 | 11/2002 | Uchiyama et al. | |
| 6,485,418 B2 | 11/2002 | Yasushi et al. | |
| 6,542,081 B2 | 4/2003 | Torch | |
| 6,575,902 B1 | 6/2003 | Burton | |
| 6,603,999 B2 | 8/2003 | SerVaas | |
| 6,663,572 B2 | 12/2003 | Starobin et al. | |
| 6,668,221 B2 | 12/2003 | Harter, Jr. et al. | |
| 6,697,723 B2 | 2/2004 | Olsen et al. | |
| 6,734,799 B2 | 5/2004 | Munch | |
| 6,791,462 B2 | 9/2004 | Choi | |
| 6,809,643 B1 | 10/2004 | Elrod et al. | |
| 6,810,309 B2 | 10/2004 | Sadler et al. | |
| 6,822,573 B2 | 11/2004 | Basir et al. | |
| 6,876,949 B2 | 4/2005 | Hilliard et al. | |
| 6,909,947 B2 | 6/2005 | Douros et al. | |
| 6,950,027 B2 | 9/2005 | Banas | |
| 6,974,414 B2 | 12/2005 | Victor | |
| 6,993,378 B2 | 1/2006 | Wiederhold et al. | |
| 7,032,705 B2 | 4/2006 | Zheng et al. | |
| 7,046,128 B2 | 5/2006 | Roberts | |
| 7,062,313 B2 | 6/2006 | Nissila | |
| 7,092,849 B2 | 8/2006 | Lafitte et al. | |
| 7,102,495 B2 | 9/2006 | Mattes et al. | |
| 7,138,938 B1 | 11/2006 | Prakah-Asante et al. | |
| 7,147,601 B2 | 12/2006 | Marks et al. | |
| 7,149,653 B2 | 12/2006 | Bihler et al. | |
| 7,183,930 B2 | 2/2007 | Basir et al. | |
| 7,183,932 B2 | 2/2007 | Bauer | |
| 7,196,629 B2 | 3/2007 | Ruoss et al. | |
| 7,219,923 B2 | 5/2007 | Fujita et al. | |
| 7,225,013 B2 | 5/2007 | Geva et al. | |
| 7,248,997 B2 | 7/2007 | Nagai et al. | |
| 7,254,439 B2 | 8/2007 | Misczynski et al. | |
| 7,266,430 B2 | 9/2007 | Basson et al. | |
| 7,283,056 B2 | 10/2007 | Bukman et al. | |
| 7,301,465 B2 | 11/2007 | Tengshe et al. | |
| 7,304,580 B2 | 12/2007 | Sullivan et al. | |
| 7,330,570 B2 | 2/2008 | Sogo et al. | |
| 7,349,792 B2 | 3/2008 | Durand | |
| 7,350,608 B2 | 4/2008 | Fernandez | |
| 7,389,178 B2 | 6/2008 | Raz et al. | |
| 7,401,233 B2 | 7/2008 | Duri et al. | |
| 7,403,804 B2 | 7/2008 | Ridder et al. | |
| 7,424,357 B2 | 9/2008 | Ozaki et al. | |
| 7,424,414 B2 | 9/2008 | Craft | |
| 7,465,272 B2 | 12/2008 | Kriger | |
| 7,482,938 B2 | 1/2009 | Suzuki | |
| 7,496,457 B2 | 2/2009 | Fujita et al. | |
| 7,502,152 B2 | 3/2009 | Lich et al. | |
| 7,507,207 B2 | 3/2009 | Sakai et al. | |
| 7,511,833 B2 | 3/2009 | Breed | |
| 7,517,099 B2 | 4/2009 | Hannah | |
| 7,532,964 B2 | 5/2009 | Fujita et al. | |
| 7,561,054 B2 | 7/2009 | Raz et al. | |
| 7,576,642 B2 | 8/2009 | Rodemer | |
| 7,618,091 B2 | 11/2009 | Akaike et al. | |
| 7,620,521 B2 | 11/2009 | Breed et al. | |
| 7,639,148 B2 | 12/2009 | Victor | |
| 7,649,445 B2 | 1/2010 | Kuramori et al. | |
| 7,650,217 B2 | 1/2010 | Ueyama | |
| 7,663,495 B2 | 2/2010 | Haque et al. | |
| 7,672,764 B2 | 3/2010 | Yoshioka et al. | |
| 7,689,271 B1 | 3/2010 | Sullivan | |
| 7,719,431 B2 | 5/2010 | Bolourchi | |
| RE41,376 E | 6/2010 | Torch | |
| 7,756,558 B2 | 7/2010 | Ridder et al. | |
| 7,769,499 B2 | 8/2010 | McQuade et al. | |
| 7,800,592 B2 | 9/2010 | Kerr et al. | |
| 7,803,111 B2 | 9/2010 | Kriger | |
| 7,805,224 B2 | 9/2010 | Basson et al. | |
| 7,809,954 B2 | 10/2010 | Miller et al. | |
| 7,864,039 B2 | 1/2011 | Georgeson | |
| 7,866,703 B2 | 1/2011 | Spahn et al. | |
| 7,933,315 B2 | 4/2011 | Li et al. | |
| 7,946,483 B2 | 5/2011 | Miller et al. | |
| 7,948,361 B2 | 5/2011 | Bennett et al. | |
| 7,948,387 B2 | 5/2011 | Ishida et al. | |
| 7,953,477 B2 | 5/2011 | Tulppo et al. | |
| 8,019,407 B2 | 9/2011 | Lian et al. | |
| 8,068,562 B1 | 11/2011 | Zhang et al. | |
| 8,106,783 B2 | 1/2012 | Wada et al. | |
| 8,140,241 B2 | 3/2012 | Takeda et al. | |
| 8,157,730 B2 | 4/2012 | LeBoeuf et al. | |
| 8,251,447 B2 | 8/2012 | Fujita et al. | |
| 8,315,757 B2 | 11/2012 | Yamamura et al. | |
| 8,328,690 B2 | 12/2012 | Ohtsu | |
| 8,428,821 B2 | 4/2013 | Nilsson | |
| 8,471,909 B2 | 6/2013 | Ishikawa | |
| 8,497,774 B2 | 7/2013 | Scalisi et al. | |
| 8,698,639 B2 | 4/2014 | Fung et al. | |
| 8,706,204 B2 | 4/2014 | Seo | |
| 8,764,676 B2 | 7/2014 | Prakash et al. | |
| 8,773,239 B2 | 7/2014 | Phillips et al. | |
| 8,886,294 B2 | 11/2014 | Lisogurski et al. | |
| 8,930,145 B2 | 1/2015 | Li et al. | |
| 8,983,732 B2 | 3/2015 | Lisseman et al. | |
| 9,149,231 B2 | 10/2015 | Fujita | |
| 9,751,534 B2 | 9/2017 | Fung et al. | |
| 2002/0005778 A1 | 1/2002 | Breed | |
| 2002/0097145 A1 | 7/2002 | Tumey | |
| 2002/0156364 A1* | 10/2002 | Madore | G01R 33/5611 |
| | | | 600/410 |
| 2002/0176511 A1* | 11/2002 | Fullerton | H04B 1/71635 |
| | | | 375/285 |

(56) References Cited

U.S. PATENT DOCUMENTS

| | | |
|---|---|---|
| 2003/0062768 A1 | 4/2003 | Loudon et al. |
| 2003/0149354 A1 | 8/2003 | Bakharev |
| 2003/0171684 A1 | 9/2003 | Vasin et al. |
| 2003/0212336 A1 | 11/2003 | Lee et al. |
| 2004/0032957 A1 | 2/2004 | Mansy et al. |
| 2004/0044293 A1 | 3/2004 | Burton |
| 2004/0088095 A1 | 5/2004 | Eberle et al. |
| 2004/0133082 A1 | 7/2004 | Abraham-Fuchs et al. |
| 2004/0245036 A1 | 12/2004 | Fujita et al. |
| 2005/0022606 A1 | 2/2005 | Partin et al. |
| 2005/0030184 A1 | 2/2005 | Victor |
| 2005/0033189 A1 | 2/2005 | McCraty et al. |
| 2005/0058456 A1 | 3/2005 | Yoo |
| 2005/0080533 A1 | 4/2005 | Basir et al. |
| 2005/0148894 A1 | 7/2005 | Misczynski et al. |
| 2005/0155808 A1 | 7/2005 | Braeuchle et al. |
| 2005/0156457 A1 | 7/2005 | Breed et al. |
| 2005/0242808 A1* | 11/2005 | McKendry ............ G01N 24/085 324/307 |
| 2005/0246134 A1 | 11/2005 | Nagai et al. |
| 2005/0256414 A1 | 11/2005 | Kettunen et al. |
| 2006/0082437 A1 | 4/2006 | Yuhara |
| 2006/0122478 A1 | 6/2006 | Sliepen et al. |
| 2006/0161322 A1 | 7/2006 | Njoku |
| 2006/0180764 A1 | 8/2006 | Yajima et al. |
| 2006/0208169 A1 | 9/2006 | Breed et al. |
| 2006/0212195 A1 | 9/2006 | Veith et al. |
| 2006/0283652 A1 | 12/2006 | Yanai et al. |
| 2006/0287605 A1 | 12/2006 | Lin et al. |
| 2007/0159344 A1 | 7/2007 | Kisacanin |
| 2007/0190970 A1 | 8/2007 | Watson |
| 2007/0237218 A1* | 10/2007 | Walker ................ H04L 27/2035 375/229 |
| 2007/0243854 A1 | 10/2007 | Taki et al. |
| 2007/0265540 A1 | 11/2007 | Fuwamoto et al. |
| 2007/0299910 A1 | 12/2007 | Fontenot et al. |
| 2008/0015422 A1 | 1/2008 | Wessel |
| 2008/0027337 A1 | 1/2008 | Dugan et al. |
| 2008/0027341 A1 | 1/2008 | Sackner et al. |
| 2008/0033518 A1 | 2/2008 | Rousso et al. |
| 2008/0040004 A1 | 2/2008 | Breed |
| 2008/0046150 A1 | 2/2008 | Breed |
| 2008/0071177 A1 | 3/2008 | Yanagidaira et al. |
| 2008/0146892 A1 | 6/2008 | LeBoeuf et al. |
| 2008/0167757 A1 | 7/2008 | Kanevsky et al. |
| 2008/0183388 A1 | 7/2008 | Goodrich |
| 2008/0195261 A1 | 8/2008 | Breed |
| 2008/0228046 A1 | 9/2008 | Futatsuyama et al. |
| 2008/0290644 A1 | 11/2008 | Spahn et al. |
| 2008/0294015 A1 | 11/2008 | Tsuji |
| 2008/0312376 A1* | 12/2008 | Mas ..................... C08G 63/664 525/61 |
| 2008/0312796 A1 | 12/2008 | Matsuura et al. |
| 2008/0319602 A1 | 12/2008 | McClellan et al. |
| 2009/0027261 A1* | 1/2009 | Martin .................... G01S 19/07 342/357.44 |
| 2009/0040054 A1 | 2/2009 | Wang et al. |
| 2009/0046538 A1 | 2/2009 | Breed et al. |
| 2009/0054751 A1 | 2/2009 | Babashan et al. |
| 2009/0091435 A1 | 4/2009 | Bolourchi |
| 2009/0156988 A1 | 6/2009 | Ferren et al. |
| 2009/0209829 A1 | 8/2009 | Yanagidaira et al. |
| 2009/0234552 A1 | 9/2009 | Takeda et al. |
| 2009/0268022 A1 | 10/2009 | Omi |
| 2009/0284361 A1 | 11/2009 | Boddie et al. |
| 2009/0289780 A1 | 11/2009 | Tenorio-Fox |
| 2009/0313987 A1 | 12/2009 | Tu |
| 2009/0315767 A1 | 12/2009 | Scalisi et al. |
| 2009/0318777 A1 | 12/2009 | Kameyama |
| 2009/0326399 A1 | 12/2009 | Batalloso et al. |
| 2010/0009808 A1 | 1/2010 | Ohtsu |
| 2010/0030043 A1 | 2/2010 | Kuhn |
| 2010/0049068 A1 | 2/2010 | Fuwamoto et al. |
| 2010/0066137 A1 | 3/2010 | Sakai et al. |
| 2010/0106365 A1 | 4/2010 | Visconti et al. |
| 2010/0113950 A1 | 5/2010 | Lin et al. |
| 2010/0148923 A1 | 6/2010 | Takizawa |
| 2010/0155609 A1* | 6/2010 | Silva .......................... G01S 7/00 250/363.06 |
| 2010/0160794 A1 | 6/2010 | Banet et al. |
| 2010/0168527 A1 | 7/2010 | Zumo et al. |
| 2010/0185101 A1 | 7/2010 | Sakai et al. |
| 2010/0217102 A1 | 8/2010 | LeBoeuf et al. |
| 2010/0222687 A1 | 9/2010 | Thijs et al. |
| 2010/0234692 A1 | 9/2010 | Kuo et al. |
| 2010/0250044 A1 | 9/2010 | Alasry et al. |
| 2010/0295707 A1 | 11/2010 | Bennie et al. |
| 2011/0009754 A1 | 1/2011 | Wenzel et al. |
| 2011/0028857 A1 | 2/2011 | Ibanez et al. |
| 2011/0034912 A1 | 2/2011 | De Graff et al. |
| 2011/0046498 A1 | 2/2011 | Klap et al. |
| 2011/0046970 A1 | 2/2011 | Fontenot |
| 2011/0066007 A1 | 3/2011 | Banet et al. |
| 2011/0066042 A1 | 3/2011 | Pandia |
| 2011/0109462 A1 | 5/2011 | Deng et al. |
| 2011/0112442 A1 | 5/2011 | Meger et al. |
| 2011/0137200 A1 | 6/2011 | Yin et al. |
| 2011/0152701 A1 | 6/2011 | Buxi et al. |
| 2011/0169625 A1 | 7/2011 | James |
| 2011/0213511 A1 | 9/2011 | Visconti et al. |
| 2011/0246028 A1 | 10/2011 | Lisseman et al. |
| 2011/0284304 A1 | 11/2011 | Van Schoiack |
| 2011/0314737 A1 | 12/2011 | Schindhelm et al. |
| 2012/0010514 A1 | 1/2012 | Vrazic |
| 2012/0022392 A1 | 1/2012 | Leuthardt et al. |
| 2012/0054054 A1 | 3/2012 | Kameyama |
| 2012/0071775 A1 | 3/2012 | Osorio et al. |
| 2012/0083668 A1 | 4/2012 | Pradeep et al. |
| 2012/0097472 A1 | 4/2012 | Kubo et al. |
| 2012/0116198 A1 | 5/2012 | Veen et al. |
| 2012/0123806 A1 | 5/2012 | Schumann, Jr. et al. |
| 2012/0212353 A1 | 8/2012 | Fung et al. |
| 2012/0215403 A1 | 8/2012 | Tengler et al. |
| 2012/0259181 A1 | 10/2012 | Fujita et al. |
| 2012/0271513 A1 | 10/2012 | Yoneda et al. |
| 2012/0290215 A1 | 11/2012 | Adler et al. |
| 2013/0030256 A1 | 1/2013 | Fujita et al. |
| 2013/0038735 A1 | 2/2013 | Nishiguchi et al. |
| 2013/0046154 A1 | 2/2013 | Lin et al. |
| 2013/0060480 A1 | 3/2013 | Korhonen et al. |
| 2013/0124038 A1 | 5/2013 | Naboulsi |
| 2013/0158741 A1 | 6/2013 | Hahne |
| 2013/0172771 A1 | 7/2013 | Muhlsteff |
| 2013/0179163 A1 | 7/2013 | Herbig et al. |
| 2013/0183646 A1 | 7/2013 | Lusted et al. |
| 2013/0204466 A1 | 8/2013 | Ricci |
| 2013/0245886 A1 | 9/2013 | Fung et al. |
| 2013/0261415 A1 | 10/2013 | Ashe et al. |
| 2013/0296666 A1 | 11/2013 | Kumar et al. |
| 2014/0039330 A1 | 2/2014 | Seo et al. |
| 2014/0058217 A1 | 2/2014 | Giovangrandi |
| 2014/0073963 A1 | 3/2014 | Engelbrecht et al. |
| 2014/0093244 A1 | 4/2014 | Zheng et al. |
| 2014/0121927 A1 | 5/2014 | Hanita |
| 2014/0148988 A1 | 5/2014 | Lathrop et al. |
| 2014/0163374 A1 | 6/2014 | Ogasawara et al. |
| 2014/0188770 A1 | 7/2014 | Agrafioti et al. |
| 2014/0224040 A1 | 8/2014 | Van'tZelfde et al. |
| 2014/0228649 A1 | 8/2014 | Rayner et al. |
| 2014/0275854 A1 | 9/2014 | Venkatraman et al. |
| 2014/0275886 A1 | 9/2014 | Teixeira |
| 2014/0303899 A1 | 10/2014 | Fung et al. |
| 2014/0309789 A1 | 10/2014 | Ricci |
| 2014/0309893 A1 | 10/2014 | Ricci |
| 2015/0148691 A1 | 5/2015 | Moyer et al. |

FOREIGN PATENT DOCUMENTS

| | | |
|---|---|---|
| DE | 10126224 | 12/2002 |
| DE | 10248894 | 5/2004 |
| DE | 69730298 | 1/2005 |
| DE | 102004045677 | 7/2005 |
| DE | 102004037298 | 3/2006 |
| DE | 102005020847 | 11/2006 |

(56) References Cited

FOREIGN PATENT DOCUMENTS

| | | |
|---|---|---|
| DE | 102006050017 | 4/2008 |
| DE | 102008042342 | 4/2010 |
| DE | 102009051260 | 6/2010 |
| DE | 102010013243 | 9/2011 |
| DE | 202012001096 | 5/2012 |
| DE | 102012208644 | 5/2013 |
| DE | 102012102459 | 9/2013 |
| DE | 102012020901 | 4/2014 |
| DE | 102013200777 | 7/2014 |
| DE | 102013010928 | 12/2014 |
| EP | 1661511 | 5/2006 |
| EP | 2426012 | 3/2012 |
| EP | 2591969 | 5/2013 |
| EP | 2675686 | 12/2013 |
| FR | 2880166 | 6/2006 |
| GB | 2465439 | 5/2010 |
| JP | 58149101 | 9/1983 |
| JP | 06107032 | 4/1994 |
| JP | 9216567 | 8/1997 |
| JP | 11105579 | 4/1999 |
| JP | 11151231 | 6/1999 |
| JP | 11328593 | 11/1999 |
| JP | 200057479 | 2/2000 |
| JP | 2000261880 | 9/2000 |
| JP | 2001151137 | 6/2001 |
| JP | 2001260698 | 9/2001 |
| JP | 2002102188 | 4/2002 |
| JP | 2004246708 | 9/2004 |
| JP | 2005168908 | 6/2005 |
| JP | 3687356 | 8/2005 |
| JP | 200614765 | 1/2006 |
| JP | 3757684 | 3/2006 |
| JP | 2006182277 | 7/2006 |
| JP | 2006302206 | 11/2006 |
| JP | 3862192 | 12/2006 |
| JP | 2006346109 | 12/2006 |
| JP | 2007229116 | 9/2007 |
| JP | 2007244479 | 9/2007 |
| JP | 2008181327 | 8/2008 |
| JP | 2008229091 | 10/2008 |
| JP | 2008305096 | 12/2008 |
| JP | 2009080718 | 4/2009 |
| JP | 2009101714 | 5/2009 |
| JP | 2009116693 | 5/2009 |
| JP | 2009142576 | 7/2009 |
| JP | 2009172205 | 8/2009 |
| JP | 2009202841 | 9/2009 |
| JP | 2009213779 | 9/2009 |
| JP | 4340991 | 10/2009 |
| JP | 4361011 | 11/2009 |
| JP | 2010122897 | 6/2010 |
| JP | 2010128649 | 6/2010 |
| JP | 2010128669 | 6/2010 |
| JP | 2010-143578 | 7/2010 |
| JP | 2010-186276 | 8/2010 |
| JP | 2011008457 | 1/2011 |
| JP | 201130869 | 2/2011 |
| JP | 2012212362 | 11/2012 |
| JP | 2012533474 | 12/2012 |
| KR | 20040098704 | 11/2004 |
| KR | 20050015771 | 2/2005 |
| KR | 20110127978 | 11/2011 |
| RU | 2298215 | 4/2007 |
| WO | WO02096694 | 12/2002 |
| WO | WO2004108466 | 12/2004 |
| WO | WO2007090896 | 8/2007 |
| WO | WO2009098731 | 8/2009 |
| WO | WO2009104460 | 8/2009 |
| WO | WO2011038803 | 4/2011 |
| WO | 2012115220 | 8/2012 |
| WO | WO2013113947 | 8/2013 |
| WO | 2013164724 | 11/2013 |
| WO | 2014128273 | 8/2014 |
| WO | WO2014123222 | 8/2014 |
| WO | WO2014149657 | 9/2014 |

OTHER PUBLICATIONS

Office Action of U.S. Appl. No. 14/697,593 dated Nov. 24, 2017, 60 pages.
German Search Report of DE 102016207052.5 dated Mar. 1, 2017, 9 pages.
TruTouch Technologies prototype, Driver Alcohol Detection System for Safety, www.DADSS.org, 1 page.
TruTouch Technologies: "Technology Overview" pp. 1-4, printed Apr. 27, 2015.
Press Release: "Volvo Cars conducts research into driver sensors in order to create cars that get to know their drivers", http://www.media.volvocars.com/global/en-gb/print/140898?print=1, Mar. 17, 2014.
Press Release, "Ford and MIT research study shows technological advancements reduce stress on driver," http://web.mit.edu/press/2010/ford-mit-release.html, Nov. 4, 2010. ?http://www.prnewswire.com/news-releases/ford-and-mit-reserach-study-shows-technological-advancements-reduce-stress-on-driver-106676293.html.
http://media.ford.com/article_display.cfm?article_id=36728 "Ford Research Developing Intelligent System to Help Drivers Manage Stressful Situations on the Road", Dearborn, Michigan, Jun. 27, 2012, 2 pages.
http://reflect.pst.ifi.lmu.de/ "The Reflect Project" article (1 page) and Video Link to "The Reflect Project" : http://vimeo.com/25081038, filmed in Maranello, Italy, Mar. 2011, 7 minutes, 53 seconds.
Internet Video: CEATEC new chip detects motion, heartbeats—Videos (news)—PC Advisor printed Jan. 17, 2012.
Office Action of U.S. Appl. No. 13/843,077 dated Feb. 11, 2016, 11 pages.
Office Action of U.S. Appl. No. 14/074,710 dated Jan. 21, 2016, 17 pages.
Office Action of U.S. Appl. No. 13/858,038 dated Oct. 15, 2015, 12 pages.
Office Action of U.S. Appl. No. 14/461,530 dated Jan. 14, 2016, 15 pages.
Nobata et al., Study of the Personal Authentication Technique Using ECG Signal toward Driver Recognition, 2 pages.
Office Action of U.S. Appl. No. 14/851,753 dated Dec. 21, 2016, 12 pages.
Office Action of U.S. Appl. No. 13/030,637 dated Mar. 28, 2013, 38 pages.
Office Action of U.S. Appl. No. 13/030,637 dated Aug. 7, 2013, 23 pages.
Office Action of U.S. Appl. No. 13/843,194 dated Mar. 27, 2015, 39 pages.
Office Action of U.S. Appl. No. 13/843,194 dated Sep. 24, 2015, 14 pages.
Office Action of U.S. Appl. No. 13/843,249 dated Oct. 7, 2014, 30 pages.
Office Action of U.S. Appl. No. 13/843,249 dated Apr. 28, 2015, 19 pages.
Office Action of U.S. Appl. No. 13/843,249 dated Sep. 4, 2015, 11 pages.
Office Action of U.S. Appl. No. 13/843,249 dated Nov. 24, 2015, 12 pages.
Office Action of U.S. Appl. No. 13/858,038 dated Jun. 26, 2015, 19 pages.
Office Action of U.S. Appl. No. 14/315,726 dated Sep. 9, 2015, 42 pages.
Office Action of U.S. Appl. No. 14/315,726 dated Dec. 2, 2015, 18 pages.
Office Action of U.S. Appl. No. 14/461,530 dated Oct. 2, 2015, 44 pages.
Poh, M. et al., "Advancements in Noncontact, Multiparameter Physiological Measurements Using a Webcam," IEEE Transactions on Biomedical Engineering, vol. 58, No. 1, pp. 7-11, Jan. 2011.
Poh, M. et al., "Non-contact, automated cardiac pulse measurements using video imaging and blind source separation," Optics Express, vol. 18, No. 10, pp. 10762-10774, May 10, 2010.
Wu, H. et al., "Eulerian Video Magnification for Revealing Subtle Changes in the World," MIT CSAIL, 8 pages.

(56) References Cited

OTHER PUBLICATIONS

Kong, L. et al., "Non-contact detection of oxygen saturation based on visible light imaging device using ambient light," Optics Express, vol. 21, No. 15, pp. 17464-17471, Jul. 29, 2013.
Langdale-Smith, N., Jan. 27, 2015. Video: CES 2015—Seeing Machines: The Future of Automotive Safety. https://www.youtube.com/watch?v=obPnLufAu7o.
Kavsaoğlu et al.: "A novel feature ranking algorithm for biometric recognition with PPG signals", Computers in Biology and Medicine vol. 49, 2014, pp. 1-14.
Murata et al.: "Noninvasive Biological Sensor System for Detection of Drunk Driving", IEEE Transactions on Information Technology in Biomedicine, vol. 15, No. 1, Jan. 2011.
Brown et al.: "Framework for Multivariate Selectivity Analysis, Part I: Theoretical and Practical Merits", Applied Spectroscopy, vol. 59, No. 6, 2005, pp. 787-803.
Ridder et al.: "Framework for Multivariate Selectivity Analysis, Part II: Experimental Applications", Applied Spectroscopy, vol. 59, No. 6, 2005, pp. 804-815.
Heitmann, Anneke et al., "Technologies for the monitoring and prevention of driver fatigue," Proceedings of the First International Driving Symposium on Human Factors in Driver Assessment, Training and Vehicle Design, 2001, pp. 81-86.
Kable, Greg, "Ferrari plans mind reading tech," Autocar.co.uk, Jan. 7, 2011.
Ofalt, Martin M., Jr., "Ford, MIT Partnering to Increase Driver Wellness and Safety," The College Driver.com, Jan. 24, 2010.
Reimer, Bryan et al., "An Evaluation of Driver Reactions to New Vehicle Parking Assist Technologies Developed to Reduce Driver Stress," MIT AgeLab White Paper, Nov. 4, 2010, pp. 1-26.
Boyraz, P. et al., "Multi-sensor driver drowsiness monitoring," Proceedings of the I MECH E Part D Journal of Automobile Engineering, vol. 222, No. 11, Jul. 23, 2008, pp. 1857-1878.
Wiegand et al., Development and Evaluation of a Naturalistic Observer Rating of Drowsiness Protocol; Feb. 25, 2009 retrieved from the internet, retrieved on May 14, 2012; http://scholar.lib.vt.edu/VTTI/reports/ORD_Final_Report_022509.pdf, entire document.
Serbedzija, et al. "Vehicle as a Co-Driver", 1st International Symposium on Vehicular Computing Systems, Published May 16, 2010, 7 pages.
Szondy, David "Volvo uses face recognition to help tired drivers", Mar. 18, 2014 http:www.gizmag.com/volvo-automated-driver-monitoring/31257/.
Boer, E., "Behavioral Entropy as a Measure of Driving Performance," 2001, five pages.
Eoh, H. et al., "Driving Performance Analysis of the ACAS FOT Data and Recommendations for a Driving Workload Manager," Technical Report UMTRI-2006-18, Dec. 2006, one hundred twenty-six pages. [Online] [Retrieval date unknown] Retrieved from the Internet URL:http://www.deepblue.lib.umich.edu/bitstream/2027.42/64468/1/102432.pdf.
Nakayama, O. et al., "Development of a Steering Entropy Method for Evaluating Driver Workload," SAE Technical Paper Series 1999-01-0892, Mar. 1-4, 1999, Detroit, Michigan, USA.
Vector Forces by Dr. Larry Bortner dated Aug. 21, 2004.
Press Release: "Faurecia keeps travelers fit, healthier in a heartbeat with "Active Wellness" car seat", Apr. 20, 2015.
Press Release: "Hoana Partners with Automotive Seat Manufacturer Faurecia to Introduce "Active Wellness™" at Auto Shanghai 2015", Apr. 20, 2015, http://www.hoana.com/hoana_partners_with_faurecia/.
YouTube Video Link: https://www.youtube.com/watch?feature=youtu.be&v=_1UBDFSzQ28&app=desktop, printed on Apr. 27, 2015—Faurecia at the 2015 Shanghai Auto Show.
Article: http://www.faurecia.cn/jian-kang-mai-bo-fo-ji-ya-active-wellness-zuo-yi-wei-jia-cheng-zhe-jian-kang-hu-hang, printed on Apr. 27, 2015.
Office Action of U.S. Appl. No. 14/851,753 dated Sep. 27, 2016, 95 pages.
Gircys, R. et al., "Movement Artefact Resistant Photoplethysmographic Probe", Elektronika Ir Elektrotechnika, IISN 1392-1215, vol. 20, No. 3, 2014, 4 pages.
Kuboyama, Yuta, "Motion Artifact Cancellation for Wearable Photoplethysmographic Sensor", B.S. Electrical Engineering and Computer Science, MIT, 2009, 66 pages.
Moharir, P.S. et al., "Optical Barker Codes", Electronics Letters, published May 2, 1974, vol. 10, No. 9, Mar. 28, 1974, 2 pages.
Office Action of U.S. Appl. No. 15/235,808 dated May 16, 2018, 60 pages.
Office Action of U.S. Appl. No. 14/697,593 dated May 18, 2018, 21 pages.
Office Action of U.S. Appl. No. 15/656,595 dated Oct. 2, 2018, 143 pages.
Office Action of U.S. Appl. No. 15/720,489 dated Oct. 1, 2018, 146 pages.
Extended European Search Report of related application No. EP 15811941.2 dated Aug. 3, 2018, 7 pages.
Office Action of U.S. Appl. No. 15/617,732 dated Jun. 24, 2019, 33 pages.
Office Action of U.S. Appl. No. 16/221,800 dated Aug. 29, 2019, 31 pages.

\* cited by examiner

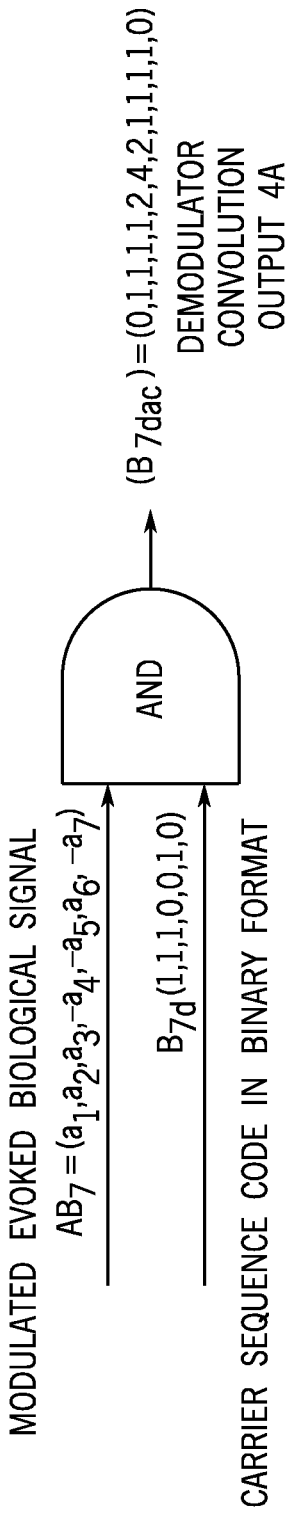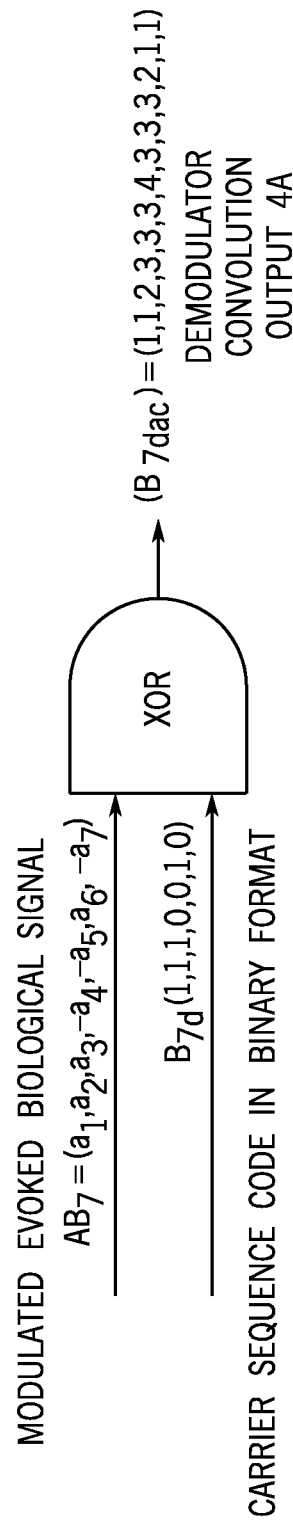
FIG. 3A
FIG. 3B

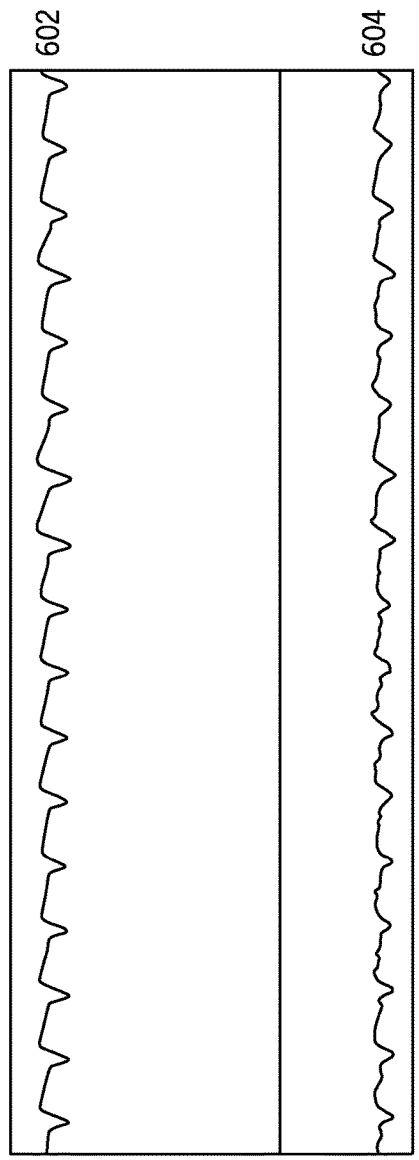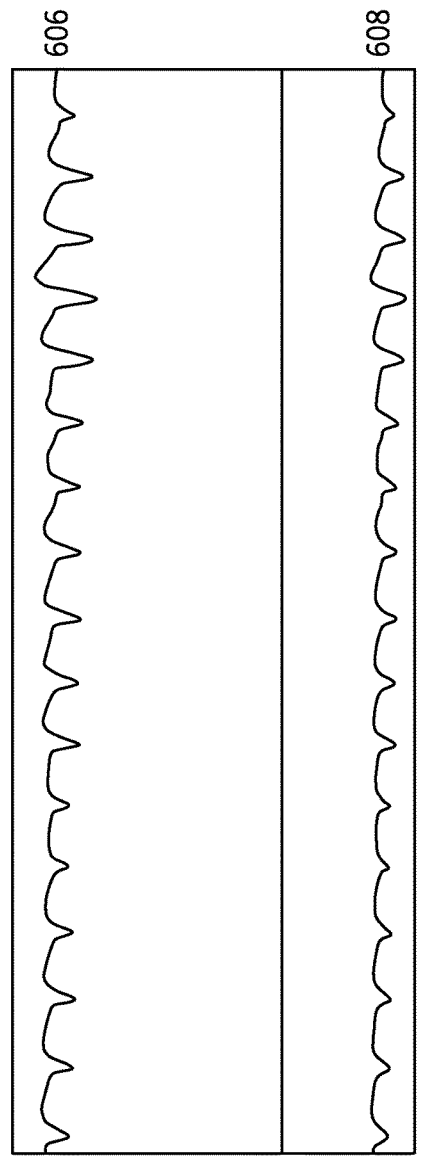

SYSTEM AND METHOD FOR BIOLOGICAL SIGNAL PROCESSING WITH HIGHLY AUTO-CORRELATED CARRIER SEQUENCES

RELATED APPLICATIONS

This applications is a continuation-in-part of U.S. application Ser. No. 14/697,593 filed on Apr. 27, 2015 and now published as U.S. 2015/0229341, which is expressly incorporated herein by reference. Further, U.S. application Ser. No. 14/697,593 is a continuation-in-part of U.S. application Ser. No. 13/858,038 filed on Apr. 6, 2013 and now published as U.S. 2014/0303899, which is also expressly incorporated herein by reference.

BACKGROUND

Biological signals are difficult to record when measured non-invasively from a body surface because the amplitude of the biological signals are low in relationship to the amplitude ambient of noise signals. Potential noise sources that can obscure measurement of biological signals from the body surface include broadcast electromagnetic radiation from electric or electronic devices, scattered electromagnetic radiation from neutral sources moving through static fields, mechanical vibrations in the environment transferring to the source and movement of the source itself, among others.

The impact of noise sources on biological signal recording can be minimized by electromechanically isolating a subject from potential interferences using electrical shielding and vibrational isolation. However, in real world applications, such control measures are not feasible and low signal recordings must be made in high noise environments. Further, the power spectrums of real world noise sources often overlap the power spectrums of the biological signal and as such are not amendable to conventional filtering techniques, such as bandpass filtering.

BRIEF DESCRIPTION

According to one aspect, a computer-implemented method for biological signal recording includes transmitting control signals from a transmitter of a sensor to a transmission source. The transmission source transmits energy towards a subject according to the control signals. The method includes receiving at a receiver of the sensor an evoked biological signal in response to energy reflection returned from the subject. The evoked biological signal is an analog signal. The method includes calculating a sampled evoked biological signal by sampling the evoked biological signal at a predetermined sampling rate. The method includes modulating the sampled evoked biological signal with a carrier sequence code resulting in a modulated evoked biological signal. The carrier sequence code has an autocorrelation function. The method includes demodulating the modulated evoked biological signal by calculating a convolution of the modulated evoked biological signal with the carrier sequence code resulting in an evoked biological signal spectrum. The evoked biological signal spectrum has a peak to sideband ratio as a function of the carrier sequence code. The method includes calculating deviations between each element of the sampled evoked biological signal and the peak to sideband ratio and filtering noise artifacts from the sampled evoked biological signal based on the deviations. Further, the method includes outputting a true evoked biological signal based on the filtering.

According to another aspect, a computer-implemented method for biological signal recording includes transmitting control signals from a transmitter of a sensor to a transmission source. The control signals are transmitted according to a carrier sequence code and the transmission source transmits energy towards a subject according to the carrier sequence code. The carrier sequence code has an auto correlation function. The method includes receiving at a receiver of the sensor an evoked biological signal in response to energy reflection returned from the subject. The evoked biological signal is an analog signal and modulated according to the carrier sequence code. The method includes demodulating the evoked biological signal by calculating a convolution of the evoked biological signal with the carrier sequence code resulting in an evoked biological signal spectrum. The evoked biological signal spectrum has signal-to-noise ratio proportional to a peak to sideband ratio. The peak to sideband ratio is a function of the carrier sequence code. Further, the method includes generating a true evoked biological signal by extracting the true evoked biological signal from the modulated evoked biological signal based on the peak to sideband ratio.

According a further aspect, a system for biological signal recording, includes a sensor including a transmitter to transmit control signals to a transmission source. The transmission source transmits energy towards a subject according to the control signals. The sensor further includes a receiver to receive an evoked biological signal in response to energy reflection returned from the subject. The evoked biological signal is an analog signal. The system also includes a system clock, communicatively coupled to the sensor, to generate a sampled evoked biological signal at a predetermined sampling rate. The system further includes a modulator, communicatively coupled to the sensor, to receive the sampled evoked biological signal and modulate the sampled evoked biological signal with a carrier sequence code having an autocorrelation function. The system includes a demodulator, communicatively coupled to the sensor, to receive the modulated evoked biological signal and demodulate the modulated evoked biological signal by calculating a convolution of the modulated evoked biological signal with the carrier sequence code resulting in an evoked biological signal spectrum. The evoked biological signal spectrum has a peak to sideband ratio as a function of the carrier sequence code. Further, the system includes a filter, communicatively coupled to the sensor, to calculate deviations between the sampled evoked biological signal and the peak to sideband ratio, filters noise artifacts from the sampled evoked biological signal based on the deviations, and outputs a true evoked biological signal based on the filtering.

According to another aspect, a system for biological signal recording includes a sensor including a transmitter to transmit control signals according to a carrier sequence code to a transmission source. The transmission source transmits energy towards a subject according to the carrier sequence code and the carrier sequence code has an autocorrelation function. The sensor further includes a receiver to receive an evoked biological signal in response to energy reflection returned from the subject. The evoked biological signal is an analog signal and modulated according to the carrier sequence code. The system includes a demodulator, communicatively coupled to the sensor, to receive the modulated evoked biological signal and demodulate the modulated evoked biological signal by calculating a convolution of the evoked biological signal with the carrier sequence code resulting in an evoked biological signal spectrum. The evoked biological signal spectrum has signal-to-noise ratio proportional to a peak to sideband ratio and the peak to sideband ratio is a function of the carrier sequence code. The demodulator generates a true evoked biological signal by extracting the true evoked biological signal from the modulated evoked biological signal based on the peak to sideband ratio.

BRIEF DESCRIPTION OF THE DRAWINGS

FIG. 3A is a schematic diagram of exemplary biological signal convolution using HACS and a logical AND gate according to an exemplary embodiment;

FIG. 3B is a schematic diagram of exemplary biological signal convolution using HACS and a logical OR gate according to an exemplary embodiment;

FIG. 6A illustrates an exemplary graphic output of measuring an evoked biological signal in a real world application without using HACS;

FIG. 6B illustrates an exemplary graphic output of measuring an evoked biological signal in a real world application using HACS and varying predetermined sampling rates.

DETAILED DESCRIPTION

Figure 1:
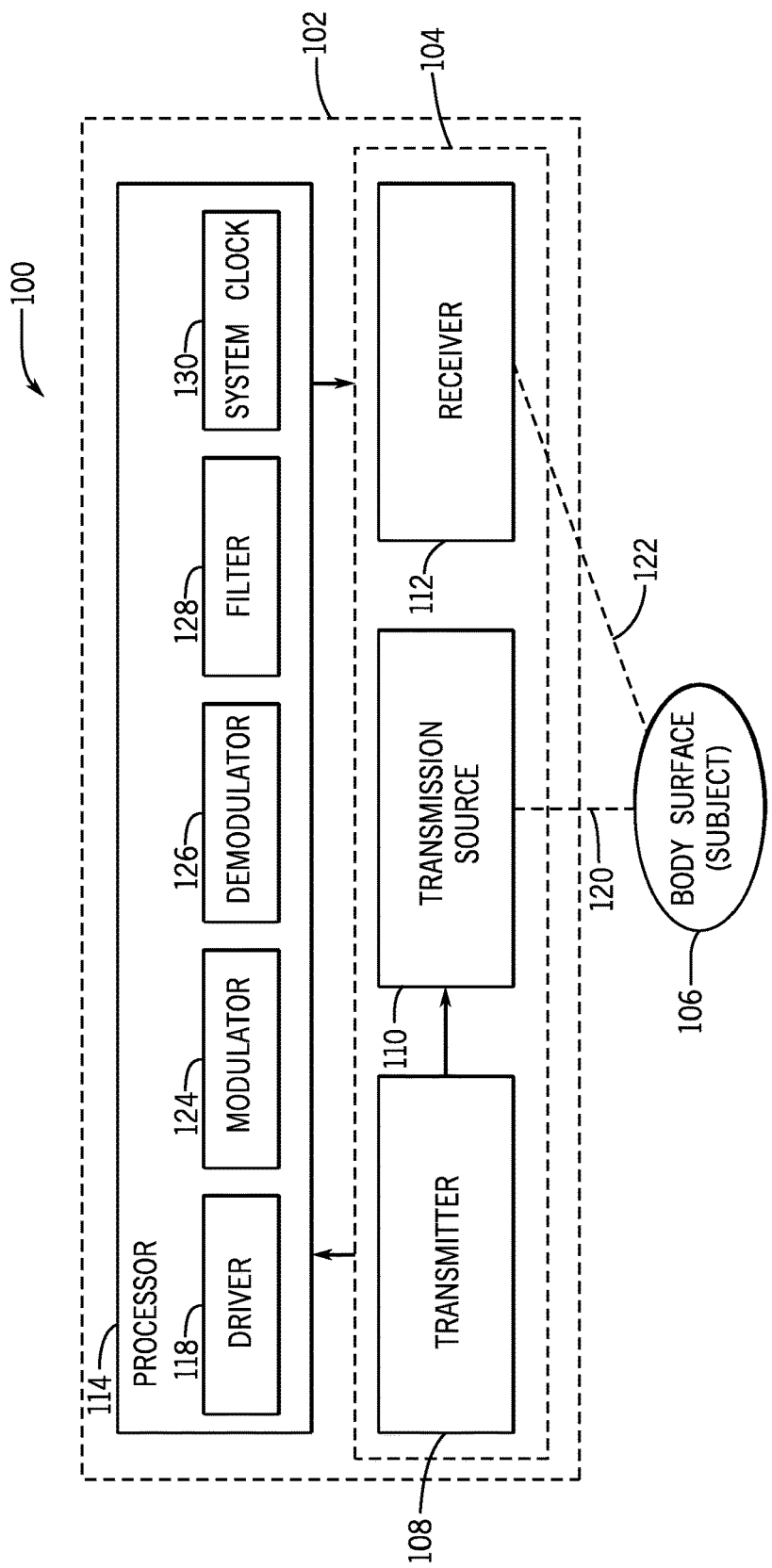
FIG. 1 is an exemplary block diagram of a system for biological signal processing using highly auto-correlated carrier sequence codes (HACS) according to an a exemplary embodiment.

The following includes definitions of selected terms employed herein. The definitions include various examples and/or forms of components that fall within the scope of a term and that can be used for implementation. The examples are not intended to be limiting. Further, the components discussed herein, can be combined, omitted or organized with other components or organized into different architectures.

"Computer communication", as used herein, refers to a communication between two or more computing devices (e.g., computer, personal digital assistant, cellular telephone, network device) and can be, for example, a network transfer, a file transfer, an applet transfer, an email, a hypertext transfer protocol (HTTP) transfer, and so on. A computer communication can occur across, for example, a wireless system (e.g., IEEE 802.11), an Ethernet system (e.g., IEEE 802.3), a token ring system (e.g., IEEE 802.5), a local area network (LAN), a wide area network (WAN), a point-to-point system, a circuit switching system, a packet switching system, among others.

"Computer-readable medium", as used herein, refers to a non-transitory medium that stores instructions and/or data. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read.

A "disk", as used herein can be, for example, a magnetic disk drive, a solid state disk drive, a floppy disk drive, a tape drive, a Zip drive, a flash memory card, and/or a memory stick. Furthermore, the disk can be a CD-ROM (compact disk ROM), a CD recordable drive (CD-R drive), a CD rewritable drive (CD-RW drive), and/or a digital video ROM drive (DVD ROM). The disk can store an operating system that controls or allocates resources of a computing device.

A "database", as used herein can refer to table, a set of tables, a set of data stores (e.g., disks) and/or methods for accessing and/or manipulating those data stores.

A "memory", as used herein can include volatile memory and/or nonvolatile memory. Non-volatile memory can include, for example, ROM (read only memory), PROM (programmable read only memory), EPROM (erasable PROM), and EEPROM (electrically erasable PROM). Volatile memory can include, for example, RAM (random access memory), synchronous RAM (SRAM), dynamic RAM (DRAM), synchronous DRAM (SDRAM), double data rate SDRAM (DDRSDRAM), and direct RAM bus RAM (DRRAM). The memory can store an operating system that controls or allocates resources of a computing device.

A "processor", as used herein, processes signals and performs general computing and arithmetic functions. Signals processed by the processor can include digital signals, data signals, computer instructions, processor instructions, messages, a bit, a bit stream, that can be received, transmitted and/or detected. Generally, the processor can be a variety of various processors including multiple single and multi-core processors and co-processors and other multiple single and multicore processor and co-processor architectures. The processor can include various modules to execute various functions.

A "vehicle," as used herein, refers to any moving vehicle that is capable of carrying one or more human occupants and is powered by any form of energy. The term "vehicle" includes, but is not limited to cars, trucks, vans, minivans, SUVs, motorcycles, scooters, boats, personal watercraft, and aircraft. In some cases, a motor vehicle includes one or more engines. Further, the term "vehicle" can refer to an electric vehicle (EV) that is capable of carrying one or more human occupants and is powered entirely or partially by one or more electric motors powered by an electric battery. The EV can include battery electric vehicles (BEV) and plug-in hybrid electric vehicles (PHEV). Additionally, the term "vehicle" can refer to an autonomous vehicle and/or self-driving vehicle powered by any form of energy. The autonomous vehicle may or may not carry one or more human occupants.

Referring now to the drawings, wherein the showings are for purposes of illustrating one or more exemplary embodiments and not for purposes of limiting same, FIG. 1 is a block diagram of a system 100 for biological signal recording using highly auto-correlated carrier sequence codes (HACS) according to an exemplary embodiment. The components FIG. 1, as well as the components of other systems, hardware architectures, and software architectures discussed herein, can be combined, omitted, or organized into different architectures for various embodiments. In some embodiments, the components of the system 100 can be implemented within a vehicle 102, for example, as discussed in U.S. application Ser. No. 14/697,593, now published as U.S. 2015/0229341, which is expressly incorporated herein by reference.

In FIG. 1, the system 100 includes a sensor 104 for measuring biological signals from a subject. In one embodiment, the sensor 104 is a sensor for detecting plethysmograph (PPG) measurements from a body surface of a subject 106. In particular, the sensor 104 can measure changes in transmission or diffused reflectance from the body surface (e.g., body tissue) of the subject 106 under active illumination. More specifically, the sensor 104 can include a transmitter 108, a transmission source 110, and a receiver 112. The sensor 104 can also include and/or be communicatively coupled to a processor 114. The processor 114 can include other components to facilitate biological signal recording as will be discussed in further detail herein.

It is understood that the system 100 can include more than one sensor 104. Further, as discussed above and detailed in U.S. application Ser. No. 14/697,593, in some embodiments, the sensor 104 can be located in a vehicle 102. For example, in some embodiments one or more sensors can be part of one or more sensor assemblies. Additionally, one or more sensors can be mechanically coupled to a vehicle seat of the vehicle 102. In other embodiments, the sensor 104 and/or the processor 114 could be integrated with a vehicle computing device, for example, a head unit (not shown).

Referring again to the sensor 104 of FIG. 1, the transmitter 108 controls the transmission source 110. More specifically, the transmitter 108 transmits control signals (not shown) to the transmission source 110 and the transmission source 110 transmits energy (e.g., a energy signal) towards the subject 106 according to the control signals. It is understood that the energy transmitted by the transmission source 110 can include, but is not limited to, light, ultrasound, sonic, and sound waves, magnetic resonance imaging using magnetic waves, electromagnetic waves, millimeter radar, computed tomography and X-ray devices using gamma rays, among others. For example, in one embodiment, which will be used as an illustrative example herein, the transmission source 110 can include at least one light emitting diode (LED) that can transmit light of a particular wavelength.

In some embodiments, the processor 114 can include a driver 118 which controls the transmitter 108 and/or the transmission source 110. In other embodiments, the driver 118 can be a component of the sensor 104 and/or the transmitter 108. The transmitter 108 and/or the driver 118 can include driver circuitry and controllers to drive the control signals to the transmission source 110 to driver energy (e.g., transmit energy (e.g., energy waves) towards the subject 106) as desired. For example, the transmitter and/or the driver 118 can cause the transmission source 110 to driver energy based on a pulsed basis or a continuous basis. In one embodiment, discussed herein, the illumination can be pulsed (e.g., blinked) according to a carrier sequence code with an autocorrelation function. In FIG. 1, the energy wave transmitted to the subject 106 is indicated by the dashed line 120.

Upon transmission of the energy wave 120 towards the subject 106, energy is reflected from the subject 106 and received by the receiver 112 to generate data signals therefrom. In FIG. 1, the reflected energy, which is an evoked biological signal, is indicated by the dashed line 122. The receiver 112 captures the reflected energy as an electrical signal in analog form. More specifically, the receiver 112 receives an evoked biological signal 122 representing a biological measurement (e.g., a PPG measurement) of the subject 106. As will be discussed herein, the receiver 112 can processes these analog signals and/or transmit the analog signals for processing to, for example, the processor 114.

With respect to the processor 114, the sensor 104 can include the processor 114 and/or the processor 114 can be included as part of another system communicatively coupled to the sensor 104. For example, the processor 114 can be part of a monitoring system (not shown) integrated with the vehicle 102. In addition to the driver 118, the processor 114 can also include a modulator 124, a demodulator 126, a filter 128, and a system clock 130. It is understood that the processor 114 can include other components not shown, for example, memory, a data store, communication interfaces, among others. It is also understood that some or all of the components of the processor 114 can be integrated with the sensor 104 and/or components of the sensor 104. It is further understood that the highly auto-correlated carrier sequence codes (HACS) used for modulation and demodulation discussed herein, can be stored at one or more of the components of the system 100.

As will be described in more detail herein, the modulator 124 facilitates modulation of the evoked biological signal 122. The demodulator 126 facilitates demodulation of the evoked biological signal 122. Further, the demodulator 126 and/or the filter 128 can generate a true biological signal from the evoked biological signal 122 free of noise artifacts that can contaminate the evoked biological signal 122. The system clock 130 controls sampling of the evoked biological signals at different sampling rates. Each of these components will be described in further detail herein.

Exemplary operation of the system 100 with reference to FIG. 1 according to an exemplary embodiment will now be described. As discussed above, in one embodiment, the system 100 includes the sensor 104 with the transmitter 108. The transmitter 108 transmits control signals to the transmission source 110. The transmission source transmits energy (i.e., energy wave 120) towards the subject 106 according to the control signals. Further, the sensor 104 includes the receiver 112 to receive an evoked biological signal 122 in response to energy reflection returned from the subject 106. The evoked biological signal 122 can be a data signal in electrical format. More specifically, the evoked biological signal 122 is an analog signal.

The evoked biological signal 122 can be contaminated by noise and motion artifacts from sources surrounding the sensor 104 and the subject 106. For example, in a vehicle setting, vibration from the vehicle 102 and other noises within and outside of the vehicle 102 can contaminate the evoked biological signal 122. In some instances, the frequencies and/or power spectrums of the noise and motion artifacts can overlap with the frequencies and/or power spectrums of the evoked biological signal 122. This overlap can cause issues in obtaining a true biological signal free of noise and motion artifacts.

Accordingly, in one embodiment, the system clock 130, which is communicatively coupled to the sensor 104, can generate a sampled evoked biological signal at a predetermined sampling rate. For example, the predetermined sampling rate can be 4 ms or less. The sampled evoked biological signal can be expressed in vector form as $A=(a_1, a_2, a_3, a_4, a_5, a_6, a_7 \ldots)$, where A represents the evoked biological signal 122 and each element in A represents $A(i_t)$, where t is the sampling rate and/or sampling interval. Modulation based on the sampled evoked biological signal can be configured to increase the amplitude of the evoked biological signal 122 in relation to noise and motion artifacts that can contaminate the evoked biological signal.

More specifically, the modulator 124, which is communicatively coupled to the sensor 104, can receive the sampled evoked biological signal and modulate the sampled evoked biological signal with a carrier sequence code having an auto correlation function. The carrier sequence code can be a highly auto-correlated carrier sequence (HACS) to process the evoked biological signal 122. Exemplary HACS include, but are not limited to, Barker codes, Frank codes, Golay codes, poly-time codes, among others. Barker codes will be used in exemplary embodiments disclosed herein, however the systems and methods discussed herein can be implemented with other types of HACS. Further, throughout the specification, a Barker code of length seven (7) will be discussed, however, it is understood that Barker codes and other carrier sequence codes of different lengths can be implemented. Furthermore, it is understood that Barker Codes and other HACS of varying lengths can be combined to produce HACS that can also be implemented in these methods and systems.

In one embodiment, the modulator 124 modulates the sampled evoked biological signal by multiplying the sampled evoked biological signal by the carrier sequence code. The number of samples in the sampled evoked biological signal is equal to the length of the carrier sequence code. As an illustrative example, seven (7) elements of the sampled evoked biological signal A, discussed above, can be multiplied with a Barker Code $B_7$ having a length of seven (7). Barker Code $B_7$ can be expressed as $B_7=(1, 1, 1, -1, -1, 1, -1)$. Accordingly, the sampled evoked biological signal multiplied by Barker Code $B_7$ results in modulation of the sampled evoked biological signal, which is expressed in vector format as $AB_7=(a_1, a_2, a_3, -a_4, -a_5, a_6, -a_7)$. Modulation of the sampled evoked biological signal can be calculated using bitwise shifting of each sampled point of the sampled evoked biological signal with the carrier sequence code. For example, $A=(a_1, a_2, a_3, a_4, a_5, a_6, a_7)$ can be multiplied by $B_7=(1, 1, 1, -1, -1, 1, -1)$ using bitwise multiplication shifting from the right.

Figure 2:
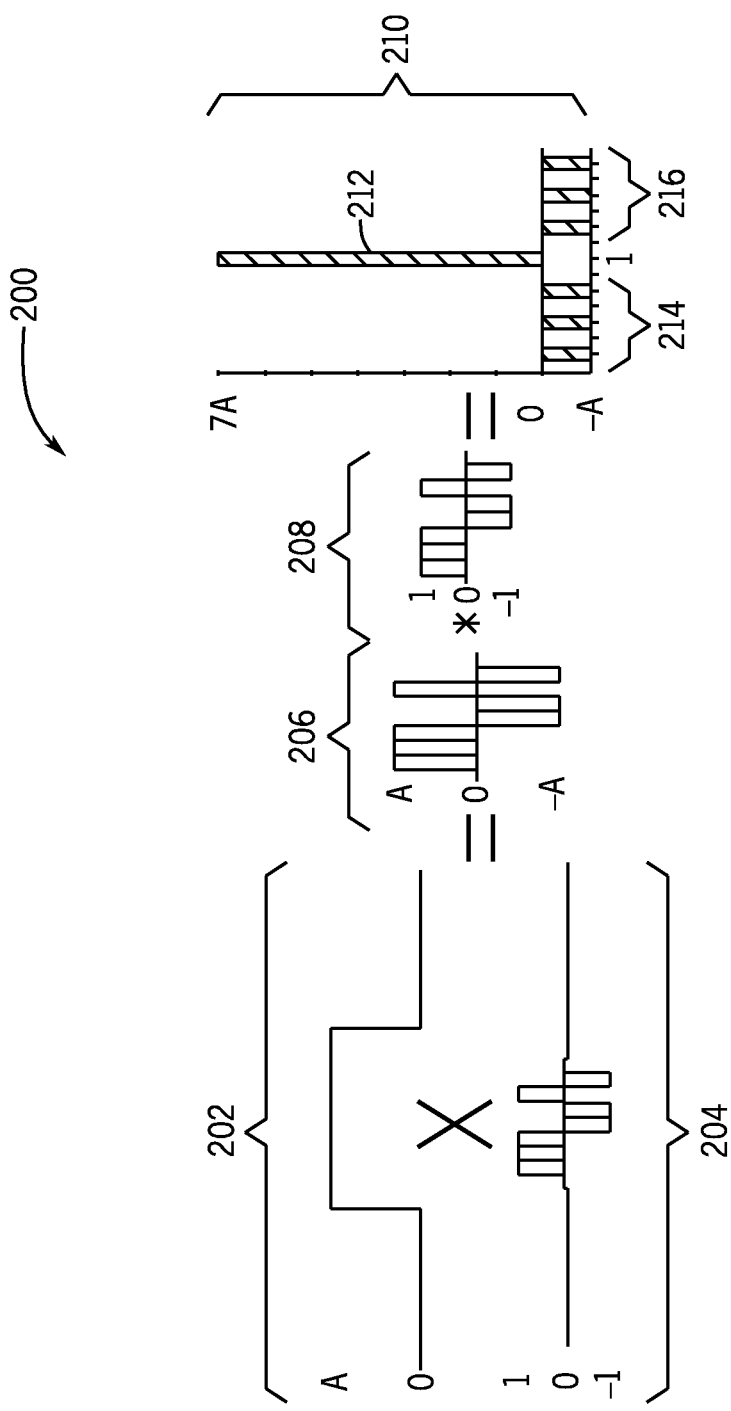
FIG. 2 is an exemplary schematic diagram of modulation and demodulation for biological signal processing using HACS according to an exemplary embodiment.

Referring now to FIG. 2, an exemplary schematic diagram of modulation and demodulation for biological signal recording using HACS according to an exemplary embodiment is shown. In this example, signal A 202 (i.e., the evoked biological signal 122) has an amplitude ½ of the noise N in the surrounding environment. Signal A 202 is modulated with the Barker Code $B_7$ 204. For example, signal A 202 is multiplied by Barker Code $B_7$ 204 resulting in a Barker segment $AB_7$ 206 (e.g., $AB_7=(a_1, a_2, a_3, -a_4, -a_5, a_6, -a_7)$). Thus, modulating the sampled evoked biological signal results in a modulated evoked biological signal with amplitude proportional to the carrier sequence code. More specifically, as shown in FIG. 2, the Barker segment $AB_7$ 206 has an amplitude ratio of +/−A.

Referring again to FIG. 1, to reconstruct a true biological signal free of noise and/or motion artifacts, the demodulator 126, which is communicatively coupled to the sensor 104, receives the modulated evoked biological signal, and demodulates the modulated evoked biological signal with the carrier sequence code. In one embodiment, the demodulator 126 calculates a convolution of the modulated evoked biological signal with the carrier sequence code. Referring again to the illustrative example discussed above and to FIG. 2, the modulated evoked biological signal is represented by Barker segment $AB_7$ 206 (i.e., $AB_7=(a_1, a_2, a_3, -a_4, -a_5, a_6, -a_7)$. The Barker segment $AB_7$ 206 is convolved with the original Barker Code $B_7$. This convolution results in an evoked biological signal spectrum. Thus, in FIG. 2, $AB_7$ 206 is convolved with Barker Code $B_7$ 208, which is the same as the original Barker code used for modulation, Barker Code $B_7$ 204. The resulting evoked biological signal spectrum is shown graphically as evoked biological signal spectrum 210.

As shown in FIG. 2, the evoked biological signal spectrum 210 has a peak to sideband ratio as a function of the carrier sequence code (i.e., in FIG. 2, the Barker Code $B_7$). Specifically, in FIG. 2, peak 212 has amplitude 7 A and there are six (6) sidebands 214, 216 on each side of the peak 212. In this example, the signal to noise ratio of the demodulated evoked biological signal is 7 A/N. As discussed above, in this example, the amplitude of signal A 204 is ½ the noise N in the environment. Thus, after demodulation, the new signal to noise ratio is 7/2=3.5.

The evoked biological signal spectrum 210 illustrated in FIG. 2 is shown quantitatively in Table 1. Table 1 represents the evoked biological signal spectrum 210 based on the convolution of $AB_7$ with $B_7$. Accordingly, as shown in Table 1, at step 7, the amplitude is 7 A. A peak to sideband ratio can be determined by calculating the absolute value of the sum at step 7 (i.e., $a_1+a_2+a_3+a_4+a_5+a_6+a_7$) divided by the sums of at steps 1, 3, 5, 9, 11, and 13 (i.e., $a_1+a_3+a_5+a_9+a_{11}+a_{13}$). This results in a peak to sideband ratio equal to 7 A/−6 A=−7/6.

TABLE 1

| Step (i) | Measured $(AB_7 * B_7)_i$ | Theoretical $(AB_7 * B_7)_i$ |
|---|---|---|
| $(AB_7 * B_7)_1$ | $-a_7$ | $-A$ |
| $(AB_7 * B_7)_2$ | $a_6 - a_7$ | 0 |
| $(AB_7 * B_7)_3$ | $-a_5 + a_6 - a_7$ | $-A$ |
| $(AB_7 * B_7)_4$ | $-a_4 - a_5 + a_6 + a_7$ | 0 |
| $(AB_7 * B_7)_5$ | $a_3 - a_4 - a_5 - a_6 + a_7$ | $-A$ |
| $(AB_7 * B_7)_6$ | $a_2 + a_3 - a_4 + a_5 - a_6 - a_7$ | 0 |
| $(AB_7 * B_7)_7$ | $a_1 + a_2 + a_3 + a_4 + a_5 + a_6 + a_7$ | 7A |
| $(AB_7 * B_7)_8$ | $a_1 + a_2 - a_3 + a_4 - a_5 - a_6$ | 0 |
| $(AB_7 * B_7)_9$ | $a_1 - a_2 - a_3 - a_4 + a_5$ | $-A$ |
| $(AB_7 * B_7)_{10}$ | $-a_1 - a_2 + a_3 + a_4$ | 0 |
| $(AB_7 * B_7)_{11}$ | $-a_1 + a_2 - a_3$ | $-A$ |
| $(AB_7 * B_7)_{12}$ | $a_1 - a_2$ | 0 |
| $(AB_7 * B_7)_{13}$ | $-a_1$ | $-A$ |

With respect to convolving the modulated evoked biological signal with the carrier sequence code, it is understood that the demodulator 126 can calculate the convolution using bitwise shifting with a logical AND gate. Further, in cases where the transmission source 110 is an LED or other pulsating device, the carrier sequence code can be converted to binary format. Specifically, the carrier sequence code can be modified to account for an ON (i.e., 1) or OFF (i.e., 0) status of the transmission source 110. Thus, in one embodiment, the modulator 124 can modulate the sampled evoked biological signal by converting the carrier sequence code to binary format and modulating the sampled evoked biological signal with the carrier sequence code in binary format. Referring again to the illustrative example, the carrier sequence code $B_7$=(1, 1, 1, −1, −1, 1, −1) can be converted to binary format as $B_{7d}$=(1,1,1,0,0,1,0). Thus, the modulator 124 can modulated the evoked biological signal by multiplying the sampled evoked biological signal by the modified carrier sequence code in binary format (i.e., $B_{7d}$=(1,1,1,0, 0,1,0)).

According to the embodiment discussed above, the demodulator 126 can demodulate the modulated evoked biological signal by calculating the convolution of the modulated evoked biological signal with the carrier sequence code in binary format, for example, using a logical AND gate. Referring again to the illustrative example, the demodulator can calculate the convolution of $B_{7d}$=(1,1,1,0, 0,1,0) with $AB_7$=($a_1$, $a_2$, $a_3$, −$a_4$, −$a_5$, $a_6$, −$a_7$) using a logical AND gate, the result of which is ($B_{7dac}$)=(0,1,1,1,2,4,2,1, 1,1,1,1,0). In this example, the resulting evoked biological signal spectrum has an amplitude of 4 A with peak adjacent sidebands of 2, and more distant sidebands of 1, and a peak to sideband ratio of 4/12. FIG. 3A of exemplary biological signal convolution using HACS and a logical AND gate according to the example described above.

In a further embodiment, and referring again to FIG. 1, the system clock 130 can calculate the sampled evoked biological signal by sampling and holding the evoked biological signal at a predetermined rate. In this embodiment, the modulator 124 can modulate the sampled evoked biological signal by multiplying the sampled evoked biological signal with the carrier sequence code using a logical XOR gate. Further, the demodulator 126 can demodulate the modulated evoked biological signal by calculating the convolution of the modulated evoked biological signal with the carrier sequence code. Referring again to the illustrative example, the demodulator can calculate the convolution of $B_{7d}$=(1,1, 1,0,0,1,0) with $AB_7$=($a_1$, $a_2$, $a_3$, −$a_4$, −$a_5$, $a_6$, −$a_7$) using a logical XOR gate, the result of which is ($B_{7dac}$)=(1,1,2,3,3, 3,4,3,3,3,2,1,1). In this example, the resulting evoked biological signal spectrum has an amplitude of 4 A with sidebands of 3, 2, or 1, and a peak to sideband ratio of 4/26. FIG. 3B is a schematic diagram of exemplary biological signal convolution using HACS and a logical XOR gate according the example described above.

Figure 4:
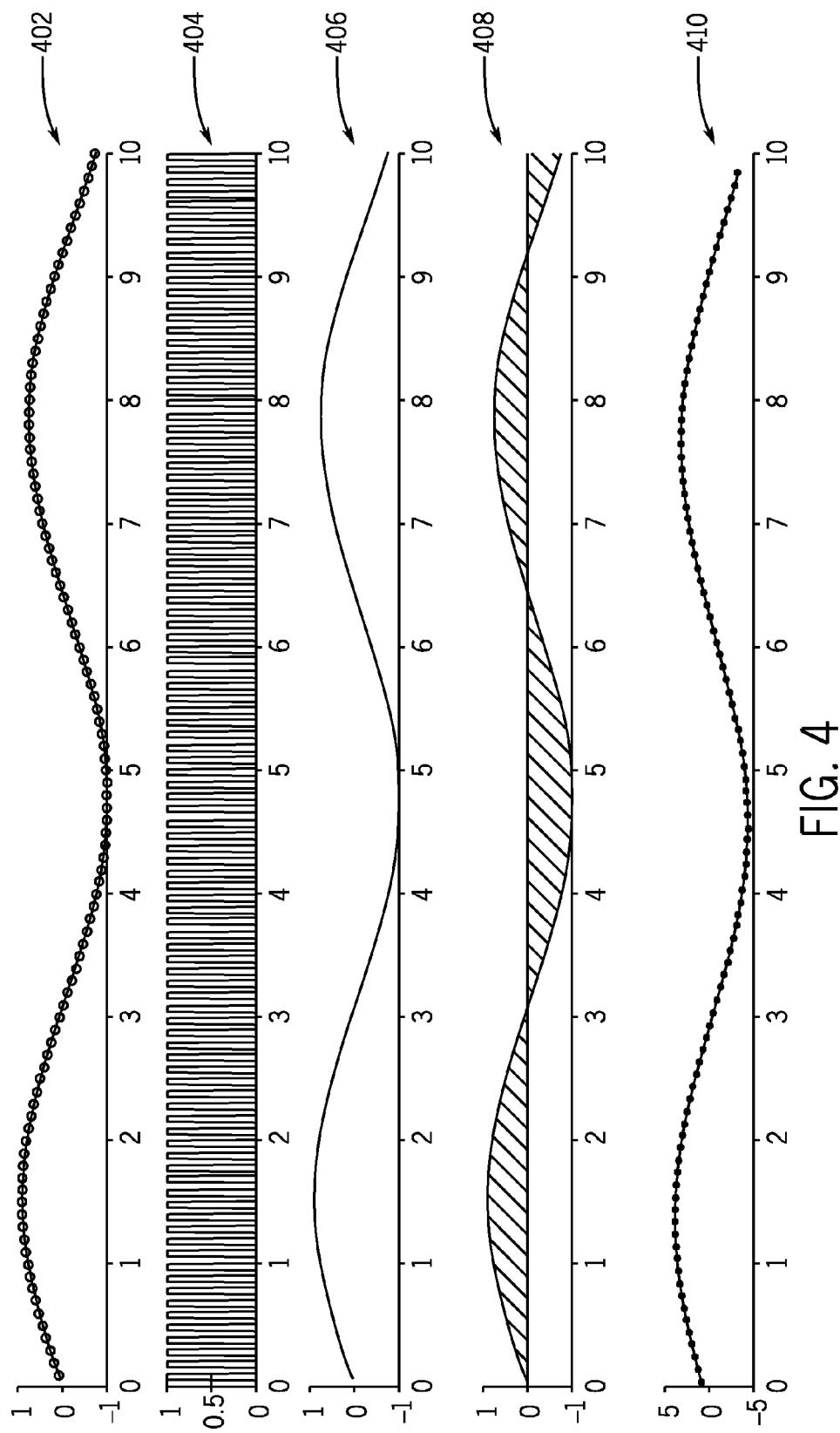
FIG. 4 is a schematic diagram of exemplary biological signal traces modulated and demodulated using HACS according to an exemplary embodiment.

The embodiment discussed in FIG. 3B is shown graphically in FIG. 4. Specifically, FIG. 4 illustrates exemplary biological signal traces modulated and demodulated using HACS according to an exemplary embodiment. Trace 402 illustrates a sinusoidal signal, for example, an evoked biological signal. The sinusoidal signal is discretized by sampling and holding the signal according to the system clock at predetermined rate shown in trace 404. The result of which is shown in trace 406. Trace 408 illustrates the modulation of the sampled evoked biological signal by multiplying the sampled evoked biological signal with the carrier sequence code using a logical XOR gate. Trace 410 illustrates the demodulation of the modulated evoked biological signal by convolving the modulated evoked biological signal with the carrier sequence code. As can be seen in trace 410, the amplification is 4 A.

Referring again to FIG. 1, based on a peak to sideband ratio, a true evoked biological signal can be reconstructed. Specifically, the filter 128 communicatively coupled to the sensor 104, can calculate deviations between the sampled evoked biological signal and the peak to sideband ratio. The filter 128 can filter and/or tune noise artifacts from the sampled evoked biological signal based on the deviations, and output a true evoked biological signal based on the filtering. For example, the filter 128 can remove elements of the sampled evoked biological signal if the respective deviation meets a predetermined threshold outside of the peak to sideband ratio. In one embodiment, the deviation of each element of the sampled evoked biological signal is compared to a predetermined threshold. The filter 128 can filter respective elements of the sampled evoked biological signal based on the comparison.

Referring again to the illustrative example shown in FIG. 2, the peak to sideband ratio is −7/6. Thus, elements of the sampled evoked biological signal that diverge more than a predetermined threshold from the peak to sideband ratio of −7/6 are rejected and removed. For example, if an element of the sampled evoked biological signal diverges more than one part in 1000 from the −7/6 peak to sideband ratio, this element is removed. In one embodiment, this element is removed and replaced with the last continuous value in the sampled evoked biological signal. Thus, a true evoked biological signal can be reconstructed by filtering out said deviations.

Figure 5:
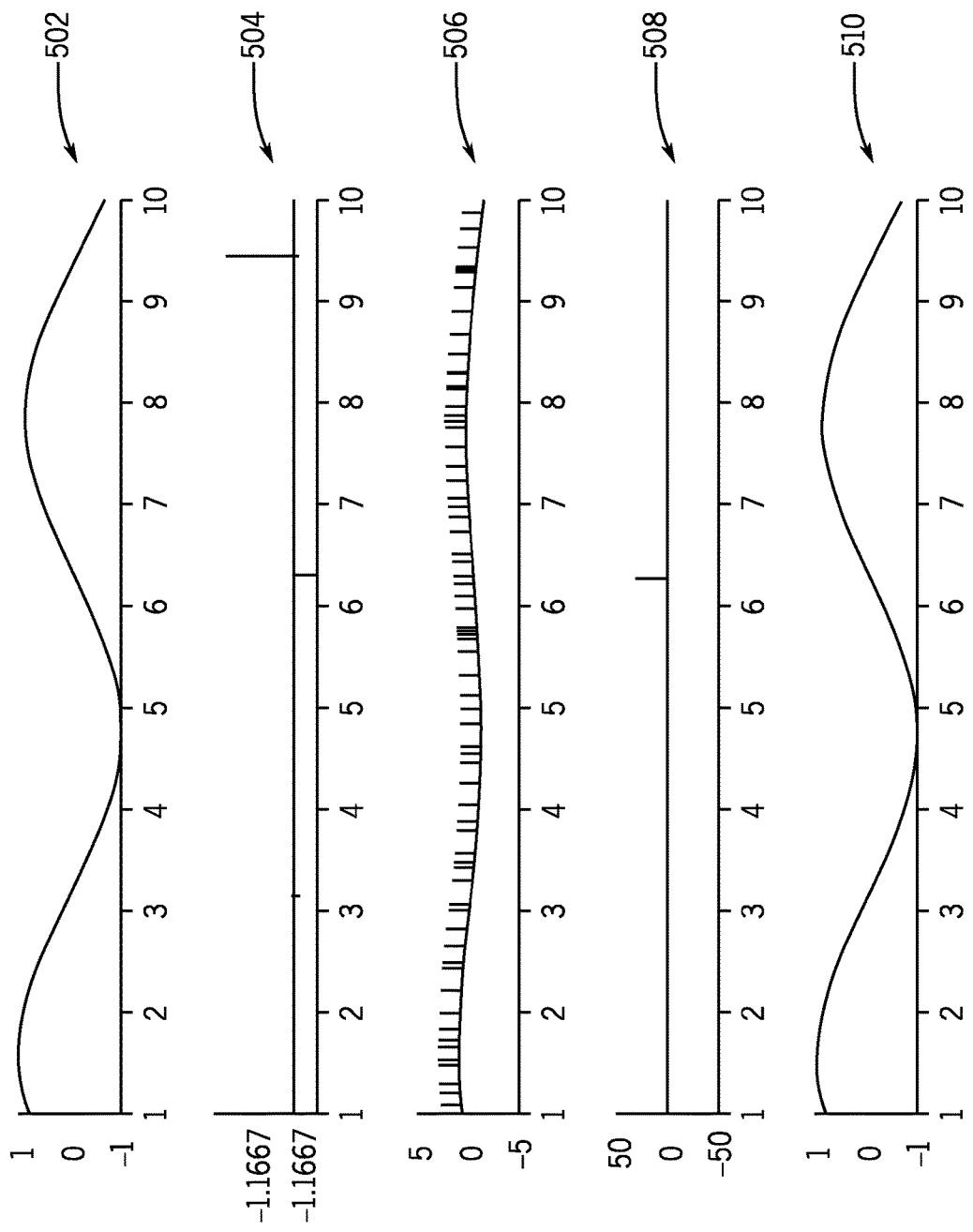
FIG. 5 is a schematic diagram of exemplary biological signal traces with simulated "spiky" noise added modulated and demodulated using HACS according to another exemplary embodiment.

Referring now to FIG. 5, an illustrative example of using HACS to filter noise using the evoked biological signal spectrum is shown. In particular, FIG. 5 illustrates exemplary biological signal traces with simulated "spiky" noise added modulated and demodulated using HACS according to another exemplary embodiment. Trace 502 illustrates a sinusoidal signal, for example, a true evoked biological signal with little to no noise. Trace 504 illustrates the evoked biological signal with noise and amplitude approximate to 2. Trace 506 illustrates the evoked biological signal spectrum with a peak to sideband ratio of −7/6. Trace 508 illustrates the introduction of spikey random noise to the signal shown in trace 502 with a divergence from the peak to sideband ratio. Based on the divergence from the peak to sideband ratio, the noise shown in trace 508 is removed and the signal shown in trace 502 is reconstructed as shown in trace 510. Similar peak to sideband deviation rejection criterion can be used with the AND and XOR logic gates of FIG. 3A and FIG. 3B to similarly reject noisy data points.

FIGS. 6A and 6B illustrate the application of HACS in a real world application. In FIG. 6A, trace 602 illustrates an evoked biological signal, a PPG signal, measured in a real world environment via direct skin contact with a sensor, which shows little noise. Trace 604 illustrates a recording of PPG signals made simultaneously with trace 602 using a non-contact sensor, thereby introducing a considerable amount of ambient noise. In FIG. 6B, trace 606 illustrates an evoked biological signal, a PPG signal, measured in a real world environment via direct skin contact with a sensor, which as can be seen, shows little noise. Trace 608 illustrates modulation and demodulation of the evoked (non-contact) biological signal at a 4 ms sampling rate using HACS. Accordingly, by varying the predetermined sampling rates, the peak to sideband ratio can be optimized, which results in less noise artifacts in the signal, for example see trace 608 as compared to trace 604. Thus, the use of HACS for recording biological signals as described herein shows the reduction of noise and/or motion artifacts to reconstruct a true biological signal.

Referring again to FIG. 1, in some embodiments, the predetermined sampling rate controlled by the system clock 130 can be varied to reduce noise in a signal. In some embodiments, the sampling rate can be tuned so that the frequency of the sample is increased and/or decreased. For example, a sampling interval of 2 ms can be tuned to a sampling rate of 4 ms. Further, the predetermined sampling rate can be held by the system clock 130 according to the peak to sideband ratio. This results in minimized sideband deviations.

Another exemplary operation of system 100 shown FIG. 1 will now be described. As discussed above, in one embodiment, the system 100 includes the sensor 104 with the transmitter 108. The transmitter 108 transmits control signals according to a carrier sequence code to the transmission source 110. Thus, the transmission source 110 transmits energy (i.e., energy wave 120) towards the subject 106 according to the carrier sequence code. The carrier sequence code has an autocorrelation function. In this embodiment, the carrier sequence code can be converted into binary format.

For example, the carrier sequence code $B_7=(1, 1, 1, -1, -1, 1, -1)$ can be converted and/or modified to binary format as $B_{7d}=(1,1,1,0,0,1,0)$. According to the binary format of the carrier sequence code, the transmission source 110 is flashed (e.g., blinked) ON (i.e., 1) and OFF (i.e., 0). Further, the sensor 104 includes the receiver 112 to receive an evoked biological signal 122 in response to energy reflection returned from the subject 106. The evoked biological signal 122 is an analog signal and modulated according to the carrier sequence code. As an illustrative example using Bid, if the transmission source 110 is ON, the output is S+N where S is the signal and N is the noise. If the transmission source is OFF, the output is N. Accordingly, the evoked biological signal modulated according to $B_{7d}$ is equal to (S+N, S+N, S+N, N, N, S+N, N).

The demodulator 126 communicatively coupled to the sensor 104, receives, the modulated evoked biological signal and demodulates the modulated evoked biological signal by calculating a convolution of the evoked biological signal with the carrier sequence code resulting in an evoked biological signal spectrum. In this example, the modulated biological signal is convolved with $B_7=(1,1,1,-1,-1,1,-1)$. The evoked biological signal spectrum has signal-to-noise ratio proportional to a peak to sideband ratio and the peak to sideband ratio is a function of the carrier sequence code. In this example, the peak to side band ratio is 4/-3, and can be expressed as 4(S+N)-3N=4S+N.

Figure 7:
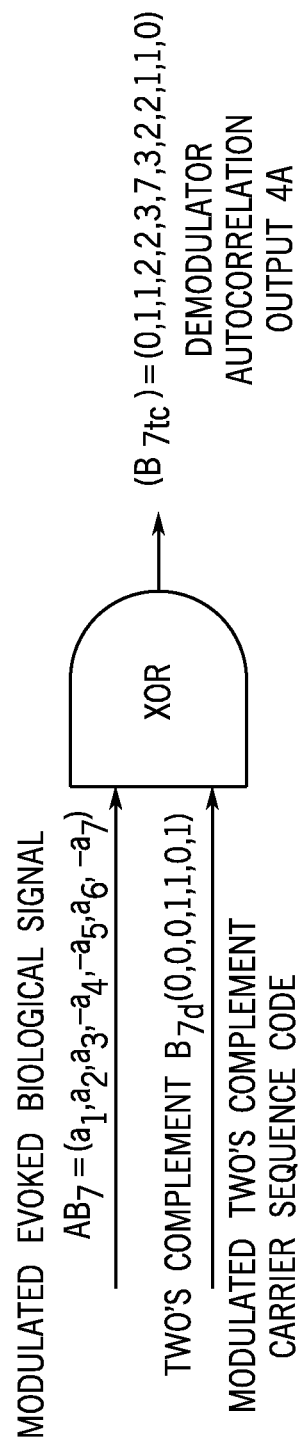
FIG. 7 is a schematic diagram of exemplary biological signal convolution using a two's complement HACS and a logical XOR gate according to an exemplary embodiment.

In another embodiment, the transmission source 110 can be flashed using the carrier sequence code and the modulated evoked biological signal can be convolved with a two's complement of the carrier sequence code. For example, the modulated biological signal is convolved using a logical XOR gate with the two's complement of $B_7=(1,1,1,-1,-1, 1,-1)$, which is $B_{7d}=(0,0,0,1,1,0,1)$. The resulting evoked biological spectrum is $B_{7tc}=(0,1,1,2,2,3,7,3,2,2,1,1,0)$. Here, the amplification is 7 A with sidebands slightly greater than 2. FIG. 7 is a schematic circuit diagram of the demodulator 126 of FIG. 1 using a logical XOR gate according the example described above.

Figure 8:
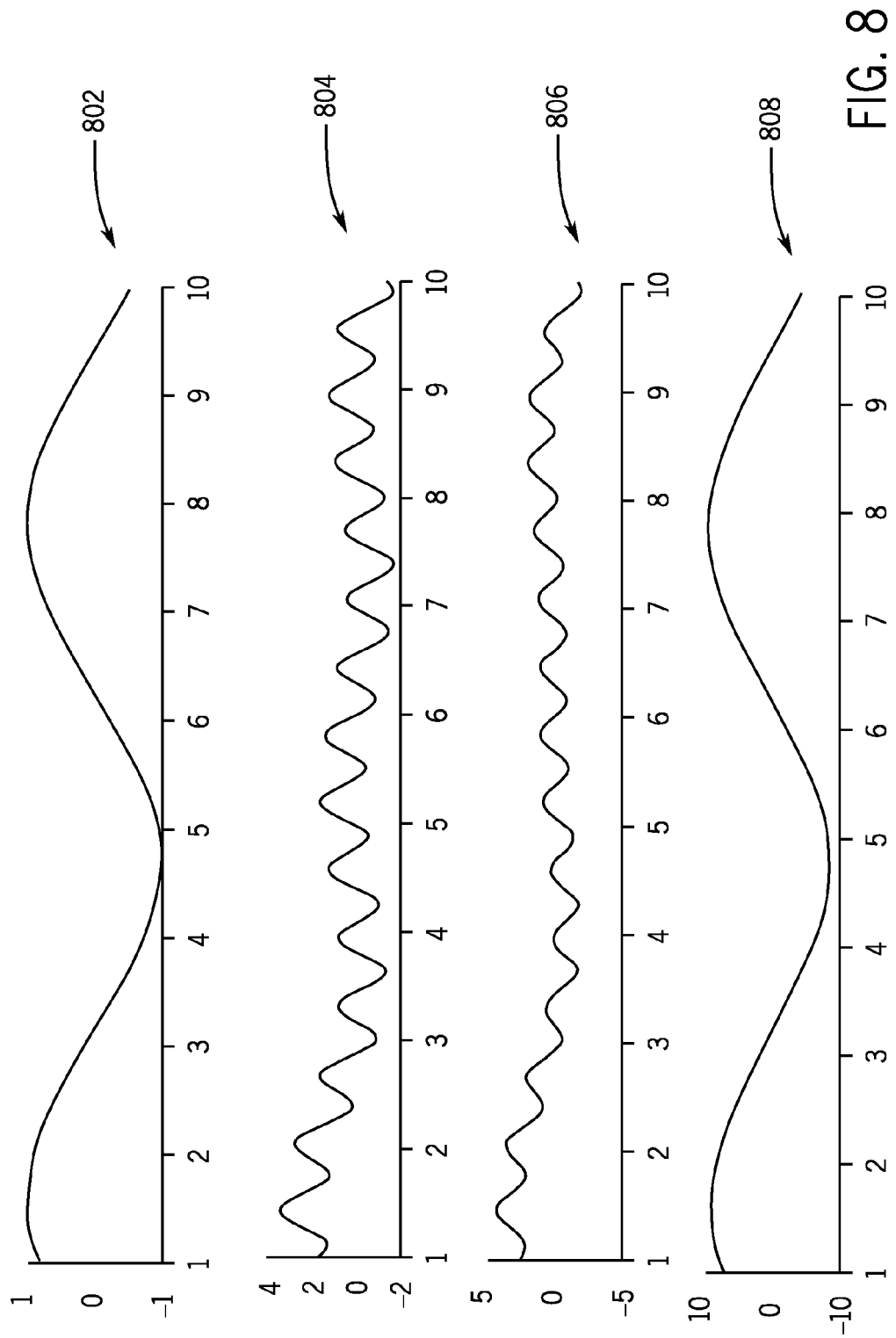
FIG. 8 is a schematic diagram of exemplary biological signal traces with sinusoidal noise sources in which sidebands of the noise overlap the sidebands of the signals, modulated and demodulated using HACS according to a further exemplary embodiment.

In a further embodiment, modulation of the carrier sequence code can use concatenation of two carrier sequences codes each having a different length. For example, the Barker code with length seven (7) can be concatenated with the Barker code of length 11. Converted into binary format, this results in $B_{711d}=(1,1,1,0,0,1,0,1,1, 1,0,0,0,1,0,0,1,0)$. Accordingly, the transmission source 110 can be flashed according the concatenated carrier sequence code in binary format. The demodulator 126 calculates the convolution of the modulated evoked biological signal with the concatenated carrier sequence code, $B_{711}=(1,1,1,-1,-1, 1,-1,1,1,1,-1,-1,1,-1,-1,1,1,-1)$. In this example, the peak to side band ratio is 9, and can be expressed as 9(S+N)-9N=9S. Thus, in this example, the system noise is completely rejected. This example is shown graphically in FIG. 8. More specifically, FIG. 8 illustrates exemplary biological signal traces with sinusoidal noise sources in which sidebands of the noise overlap the sidebands of the signals, modulated and demodulated using HACS according to a further exemplary embodiment. Trace 802 illustrates a sinusoidal signal, for example, an evoked biological signal S=sin(x). Trace 804 illustrates noise and/or motion artifacts as N=sin(0.5x)+sin(x)+sin(1.5x)+sin(10x). Trace 806 illustrates the signal with noise, S+N. Trace 808 illustrates the convolution product spectrum of the evoked biological signal with amplification of 9. The demodulator 126 and/or the filter 128 can further process the modulated evoked biological signal by generating a true evoked biological signal by extracting the true evoked biological signal from the modulated evoked biological signal based on the peak to sideband ratio.

Figure 9:
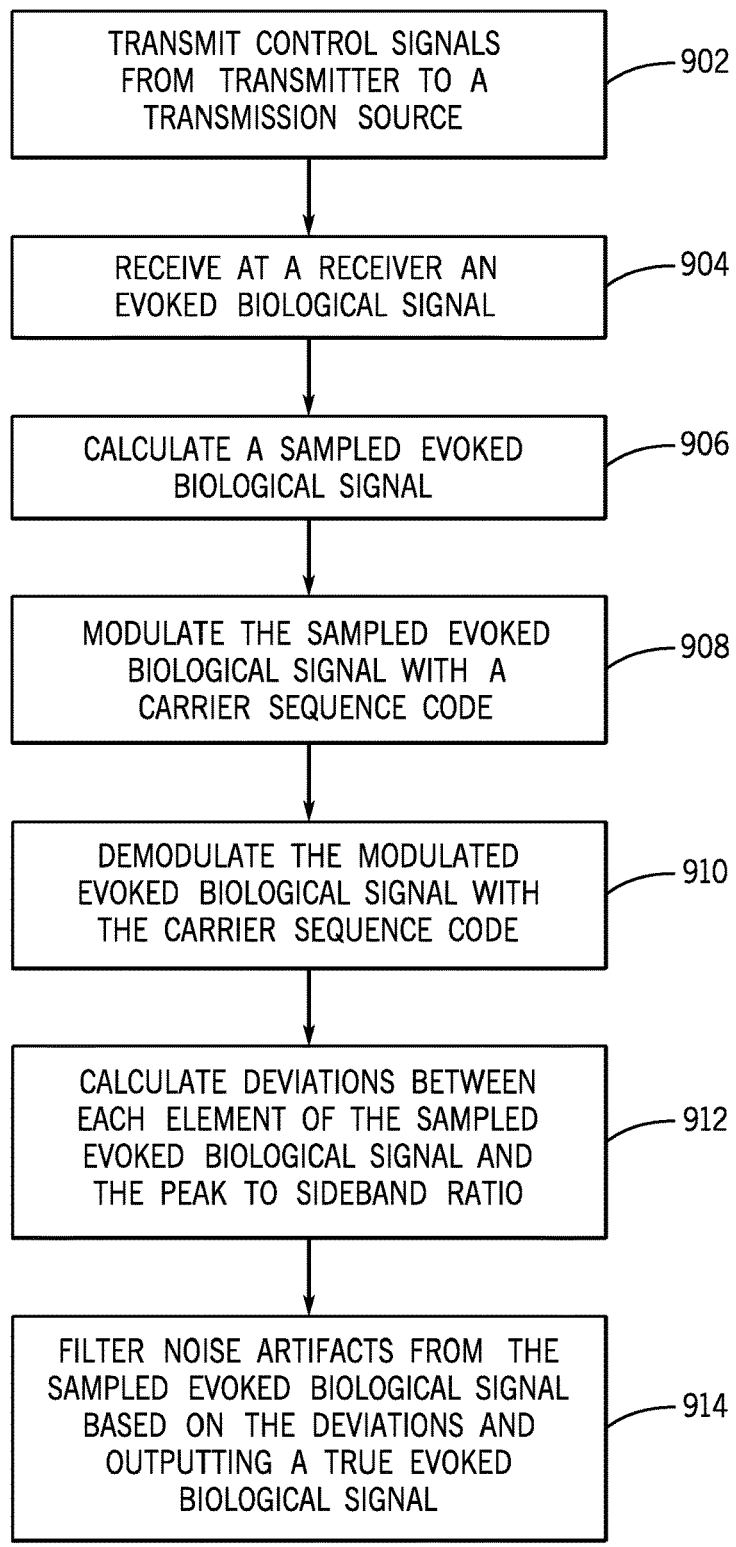
FIG. 9 is a flow diagram of an exemplary method for biological signal processing using highly auto-correlated carrier sequence codes (HACS) according to an a exemplary embodiment.

Referring now to FIG. 9, an exemplary method for biological signal recording using highly auto-correlated carrier sequence codes (HACS) according to an a exemplary embodiment will be described. FIG. 9 will be described with reference to the components of FIGS. 1-3. The methods described herein can be facilitated by the system components and examples described above. At block 902, the method includes transmitting control signals from a transmitter of a sensor to a transmission source. The transmission source transmits energy towards a subject according to the control signals. As discussed above with FIG. 1, the transmitter 108 controls the transmission source 110. More specifically, the transmitter 108 transmits control signals (not shown) to the transmission source 110 and the transmission source 110 transmits energy (e.g., a energy signal 120) towards the subject 106 according to the control signals.

At block 904, the method includes receiving at a receiver of the sensor an evoked biological signal in response to energy reflection returned from the subject. The evoked biological signal is an analog signal. As discussed above with FIG. 1, the receiver 112 receives an evoked biological signal 122 representing a biological measurement (e.g., a PPG measurement) of the subject 106. At block 906, the method includes calculating a sampled evoked biological signal by sampling the evoked biological signal at a predetermined sampling rate. The sampled evoked biological signal can be expressed in vector form as $A=(a_1, a_2, a_3, a_4, a_5, a_6, a_7 \ldots)$, where A represents the evoked biological signal 122 and each element in A represents $A(i_t)$, where t is the sampling rate and/or sampling interval. The system clock 130 controls sampling of the evoked biological signals at different sampling rates. In some embodiments, as discussed above, calculating the sampled evoked biological signal further includes sampling and holding the evoked biological signal by the system clock 130 at a predetermined rate.

Further, at block 908, the method includes modulating the sampled evoked biological signal with a carrier sequence code resulting in a modulated evoked biological signal. The carrier sequence code has an autocorrelation function. The carrier sequence code can be a highly auto-correlated carrier sequence (HACS) to process the evoked biological signal. For example, as described in the exemplary embodiments herein, the carrier sequence code can be a Barker code of length seven (7). As discussed above, in some embodiments, the modulator 124 can facilitate the modulation of the sampled evoked biological signal according to HACS. For example, the sampled evoked biological signal multiplied by Barker Code $B_7$ results in modulation of the sampled evoked biological signal, which is expressed in vector format as $AB_7=(a_1, a_2, a_3, -a_4, -a_5, a_6, -a_7)$.

As discussed above, in some embodiments, modulating the sampled evoked biological signal further includes converting the carrier sequence code to binary format and modulating the sampled evoked biological signal with the carrier sequence code in binary format. Thus, the carrier sequence code $B_7=(1, 1, 1, -1, -1, 1, -1)$ can be converted to binary format as $B_{7d}=(1,1,1,0,0,1,0)$. Additionally, in embodiments where the sampled evoked biological signal is sampled and held, modulating the sampled evoked biological signal can include multiplying the sampled evoked biological signal with the carrier sequence code using a logical XOR gate. (See FIGS. 7 and 8).

At block 910, the method includes demodulating the modulated evoked biological signal by calculating a convolution of the modulated evoked biological signal with the carrier sequence code resulting in an evoked biological signal spectrum. The evoked biological signal spectrum has a peak to sideband ratio as a function of the carrier sequence code. In other embodiments, the evoked biological signal spectrum represents the evoked biological signal with amplitude increased by a factor proportional to the peak to sideband ratio. As discussed above, according to one illustrative example, the demodulator 126 can convolve $AB_7=(a_1, a_2, a_3, -a_4, -a_5, a_6, -a_7)$ with the original Barker code used for modulation, for example, Barker Code $B_7$, which results in an evoked biological signal spectrum with a peak to sideband ratio equal to 7 A/−6.

In examples where the sampled evoked biological signal is modulated using a carrier sequence code in binary format, demodulating the modulated evoked biological signal further includes demodulating the modulated evoked biological signal by calculating the convolution of the modulated evoked biological signal with the carrier sequence code in binary format using a logical AND gate. For example, FIG. 3A illustrates exemplary biological signal convolution using HACS and a logical AND gate.

At block 912, the method includes calculating deviations between each element of the sampled evoked biological signal and the peak to sideband ratio. For example, the filter 128 can calculate deviations between the sampled evoked biological signal and the peak to sideband ratio. At block 914, the method includes filtering noise artifacts from the sampled evoked biological signal based on the deviations and outputting a true evoked biological signal based on the filtering. Thus, in one embodiment, the filter 128 can filter noise artifacts from the sampled evoked biological signal based on the deviations, and output a true evoked biological signal based on the filtering.

Figure 10:
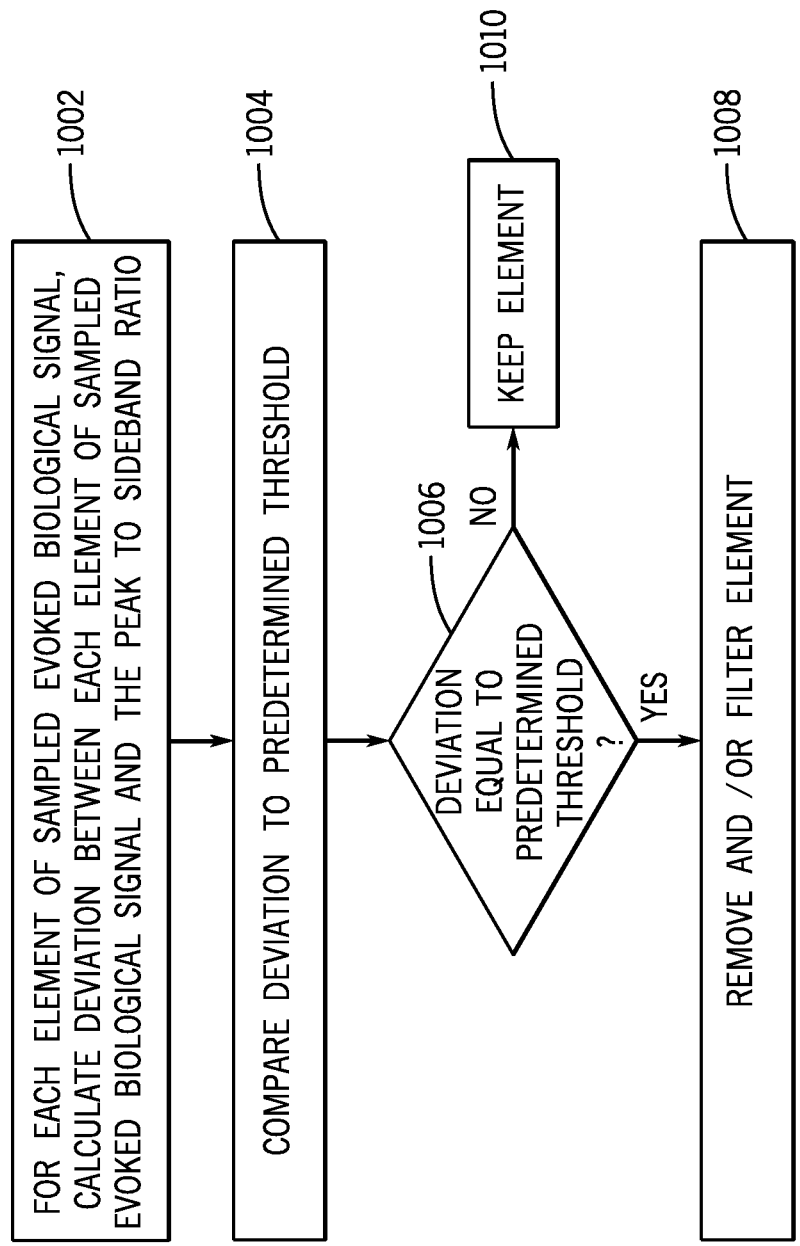
FIG. 10 is a flow diagram of an exemplary method for filtering the modulated evoked biological signal according to an exemplary embodiment.

Calculating deviations and filtering noise artifacts will now be described in more detail with reference to FIG. 10. As mentioned above, for each element of the modulated biological signal, the deviation between each element and the peak to sideband ratio is determined at block 1002. At block 1004, the deviation is compared to a predetermined threshold. At block 1006, if the deviation meets and/or equals the predetermined threshold, then at block 1008, the respective element of the sampled evoked biological signal is removed. In one embodiment, this element is removed and replaced with the last continuous value in the sampled evoked biological signal. Otherwise, at block 1010, the respective element of the sampled evoked biological signal is not removed.

Figure 11:
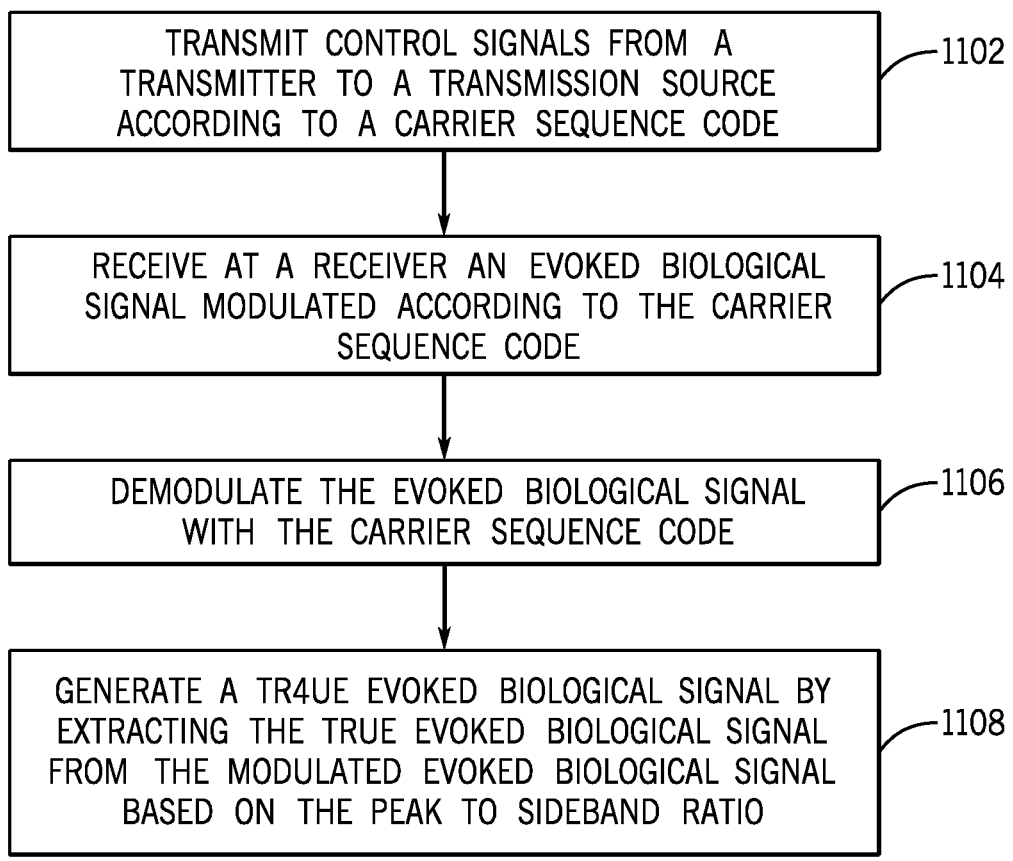
FIG. 11 is a flow diagram of a different exemplary method for biological signal processing using highly auto-correlated carrier sequence codes (HACS) according to an exemplary embodiment.

Referring now to FIG. 11, an exemplary method according to another embodiment for biological signal recording using highly auto-correlated carrier sequence codes (HACS) will be described. At block 1102, the method includes transmitting control signals from a transmitter of a sensor to a transmission source. The control signals are transmitted according to a carrier sequence code and the transmission source transmits energy towards a subject according to the carrier sequence code. The carrier sequence code has an auto correlation function. Thus, in one embodiment, transmitting control signals from the transmitter 108 of the sensor 104 to the transmission source 110 includes the control signals driving the execution and/or command (e.g., ON/OFF, blinking) of the transmission source 110 according to the carrier sequence code. In some embodiments, as discussed above, the carrier sequence code is a concatenation of two carrier sequences codes each having a different length.

At block 1104, the method includes receiving at a receiver of the sensor an evoked biological signal in response to energy reflection returned from the subject. The evoked biological signal is an analog signal and modulated according to the carrier sequence code. Thus, the sensor the sensor 104 includes the receiver 112 to receive an evoked biological signal 122 in response to energy reflection returned from the subject 106.

At block 1106, the method includes demodulating the evoked biological signal by calculating a convolution of the evoked biological signal with the carrier sequence code resulting in an evoked biological signal spectrum. The evoked biological signal spectrum has a signal-to-noise ratio proportional to a peak to sideband ratio. The peak to sideband ratio is a function of the carrier sequence code. In some embodiments, as discussed above, the carrier sequence code is a concatenation of two carrier sequences codes each having a different length. Thus, the demodulation is performed by convolving the modulated biological signal with the concatenation of two carrier sequence codes. In a further embodiment, demodulating the modulated evoked biological signal further includes demodulating the modulated evoked biological signal by calculating the convolution of the modulated evoked biological signal with a two's complement of the carrier sequence code in binary format using a logical XOR gate. (See FIG. 7). Further, at block 1108, the method includes generating a true evoked biological signal by extracting the true evoked biological signal from the modulated evoked biological signal based on the peak to sideband ratio. Accordingly, a true biological signal can be reconstructed from a noisy environment.

The embodiments discussed herein may also be described and implemented in the context of non-transitory computer-readable medium storing computer-executable instructions, as discussed above. Further, it will be appreciated that various implementations of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A computer-implemented method for biological signal recording, comprising:

transmitting control signals from a transmitter of a sensor to a transmission source, wherein the transmission source transmits energy towards a subject according to the control signals;

receiving at a receiver of the sensor an evoked biological signal in response to energy reflection returned from the subject, wherein the evoked biological signal is an analog signal;

processing a sampled evoked biological signal by sampling the evoked biological signal at a predetermined sampling rate;

modulating the sampled evoked biological signal with a carrier sequence code resulting in a modulated evoked biological signal, the carrier sequence code having an autocorrelation function;

demodulating the modulated evoked biological signal by processing a convolution of the modulated evoked biological signal with the carrier sequence code resulting in an evoked biological signal spectrum, the evoked biological signal spectrum having a peak to sideband ratio as a function of the carrier sequence code;

processing deviations between each element of the sampled evoked biological signal and the peak to sideband ratio;

filtering noise artifacts from the sampled evoked biological signal based on the processed deviations; and outputting a true evoked biological signal based on the filtering.

2. The computer-implemented method of claim 1, wherein modulating the sampled evoked biological signal further includes converting the carrier sequence code to binary format and modulating the sampled evoked biological signal with the carrier sequence code in binary format.

3. The computer-implemented method of claim 2, wherein demodulating the modulated evoked biological signal further includes demodulating the modulated evoked biological signal by processing the convolution of the modulated evoked biological signal with the carrier sequence code in binary format.

4. The computer-implemented method of claim 1, wherein processing the sampled evoked biological signal further includes sampling and holding the evoked biological signal by a system clock at a predetermined rate.

5. The computer-implemented method of claim 4, wherein modulating the sampled evoked biological signal further includes executing multiplication of the sampled evoked biological signal with the carrier sequence code.

6. The computer-implemented method of claim 4, wherein the sampled evoked biological signal further includes varying the predetermined rate of the system clock to optimize the peak to sideband ratio in the evoked biological signal spectrum.

7. The computer-implemented method of claim 1, wherein the carrier sequence code is a Barker sequence.

8. The computer-implemented method of claim 1, wherein filtering noise artifacts from the sampled evoked biological signal based on the processed deviations further includes comparing the deviation of each element of the sampled evoked biological to a predetermined threshold and filtering respective elements of the sampled evoked biological signal based on the comparison.

9. The computer-implemented method of claim 1, wherein the evoked biological signal spectrum represents the evoked biological signal with amplitude increased by a factor proportional to the peak to sideband ratio.

10. A computer-implemented method for biological signal recording, comprising:

transmitting control signals from a transmitter of a sensor to a transmission source, wherein the control signals are transmitted according to a carrier sequence code and the transmission source transmits energy towards a subject according to the carrier sequence code, the carrier sequence code having an auto correlation function;

receiving at a receiver of the sensor an evoked biological signal in response to energy reflection returned from the subject, wherein the evoked biological signal is an analog signal and modulated according to the carrier sequence code;

demodulating the evoked biological signal by processing a convolution of the evoked biological signal with the carrier sequence code resulting in an evoked biological signal spectrum, the evoked biological signal spectrum having signal-to-noise ratio proportional to a peak to sideband ratio, wherein the peak to sideband ratio is a function of the carrier sequence code;

outputting a true evoked biological signal by extracting the true evoked biological signal from the modulated evoked biological signal based on the peak to sideband ratio.

11. The computer-implemented method of claim 10, wherein transmitting control signals from the transmitter of the sensor to the transmission source further includes the control signals driving the blinking of the transmission source according to the carrier sequence code.

12. The computer-implemented method of claim 10, wherein the carrier sequence code is a concatenation of two carrier sequences codes each having a different length.

13. The computer-implemented method of claim 10, wherein demodulating the modulated evoked biological signal further includes demodulating the modulated evoked biological signal by processing the convolution of the modulated evoked biological signal with a two's complement of the carrier sequence code in binary format.

14. A system for biological signal recording, comprising:
a memory storing instructions that are executed by a processor that includes:
a sensor including a transmitter to transmit control signals to a transmission source, wherein the transmission source transmits energy towards a subject according to the control signals, the sensor further including a receiver to receive an evoked biological signal in response to energy reflection returned from the subject, wherein the evoked biological signal is an analog signal;
a system clock, communicatively coupled to the sensor, to process a sampled evoked biological signal at a predetermined sampling rate;
a modulator, communicatively coupled to the sensor, to receive the sampled evoked biological signal and modulate the sampled evoked biological signal with a carrier sequence code having an autocorrelation function;
a demodulator, communicatively coupled to the sensor, to receive the modulated evoked biological signal and demodulate the modulated evoked biological signal by processing a convolution of the modulated evoked biological signal with the carrier sequence code resulting in an evoked biological signal spectrum, the evoked biological signal spectrum having a peak to sideband ratio as a function of the carrier sequence code; and
a filter, communicatively coupled to the sensor, to process deviations between the sampled evoked biological signal and the peak to sideband ratio, filters noise artifacts from the sampled evoked biological signal based on the processed deviations, and outputs a true evoked biological signal based on the filtering.

15. The system of claim 14, wherein the demodulator further demodulates the modulated evoked biological signal by processing the convolution of the modulated evoked biological signal with the carrier sequence code in binary format.

16. The system of claim 14, wherein the filter removes elements of the sampled evoked biological signal if the respective deviation meets a predetermined threshold outside of the peak to sideband ratio.

17. A system for biological signal recording, comprising:
a memory storing instructions that are executed by a processor that includes:
a sensor including a transmitter to transmit control signals according to a carrier sequence code to a transmission source, wherein the transmission source transmits energy towards a subject according to the carrier sequence code, the carrier sequence code having an autocorrelation function,
wherein the sensor further includes a receiver to receive an evoked biological signal in response to energy reflection returned from the subject, wherein the evoked biological signal is an analog signal and modulated according to the carrier sequence code; and
a demodulator, communicatively coupled to the sensor, to receive the modulated evoked biological signal and demodulate the modulated evoked biological signal by processing a convolution of the evoked biological signal with the carrier sequence code resulting in an evoked biological signal spectrum, the evoked biological signal spectrum having signal-to-noise ratio proportional to a peak to sideband ratio, wherein the peak to sideband ratio is a function of the carrier sequence code,
wherein the demodulator outputs a true evoked biological signal by extracting the true evoked biological signal from the modulated evoked biological signal based on the peak to sideband ratio.

18. The system of claim 17, wherein the carrier sequence code is a concatenation of two carrier sequences codes each having a different length.

19. The system of claim 17, wherein demodulator further demodulates the modulated evoked biological signal by processing the convolution of the modulated evoked biological signal with a two's complement of the carrier sequence code in binary format.

20. The system of claim 17, wherein the evoked biological signal includes signal and noise elements corresponding to the carrier sequence code in binary format.

21. The system of claim 17, wherein the evoked biological signal spectrum has an amplitude increased by a factor proportional to the peak to sideband ratio.

* * * * *